(12) United States Patent
Cicciarelli et al.

(10) Patent No.: US 11,143,654 B2
(45) Date of Patent: Oct. 12, 2021

(54) METHODS AND KITS FOR SCREENING TRANSPLANT RECIPIENTS AND CANDIDATES

(71) Applicant: NATIONAL INSTITUTE OF TRANSPLANTATION FOUNDATION, Los Angeles, CA (US)

(72) Inventors: James C Cicciarelli, Rolling Hills, CA (US); Noriyuki Kasahara, Los Angeles, CA (US)

(73) Assignee: NATIONAL INSTITUTE OF TRANSPLANTATION FOUNDATION, Los Angeles, CA (US)

( * ) Notice: Subject to any disclaimer, the term of this patent is extended or adjusted under 35 U.S.C. 154(b) by 316 days.

(21) Appl. No.: 15/391,814

(22) Filed: Dec. 27, 2016

(65) Prior Publication Data

US 2017/0234875 A1     Aug. 17, 2017

Related U.S. Application Data

(63) Continuation of application No. 12/755,843, filed on Apr. 7, 2010, now Pat. No. 9,528,988.

(Continued)

(51) Int. Cl.
*G01N 33/569*    (2006.01)
*G01N 33/566*    (2006.01)
(Continued)

(52) U.S. Cl.
CPC ..... *G01N 33/56977* (2013.01); *G01N 33/564* (2013.01); *G01N 33/566* (2013.01);
(Continued)

(58) Field of Classification Search
CPC .......... G01N 33/56977; G01N 33/564; G01N 33/566; G01N 33/6893;
(Continued)

(56) References Cited

U.S. PATENT DOCUMENTS 4,868,109 A * 9/1989 Lansdorp ............. C07K 16/468
435/7.1
5,981,180 A * 11/1999 Chandler ........... G01N 15/1012
435/6.12

(Continued)

OTHER PUBLICATIONS

Pei et al. Single Human Leucocyte Antigen Flow Cytometry Beads for Accurate Identification of Human Leucocyte Antigen Antibody Specificities. Transplantation 75 (1): 43-49, (Jan. 15, 2003).*

(Continued)

*Primary Examiner* — Gailene Gabel
(74) *Attorney, Agent, or Firm* — Brian J. Pangrle

(57) ABSTRACT

Methods and kits are provided for determining of immunoglobulin isotypes and subclasses in a subject. In general the subject is a human who is a transplant candidate recipient or recipient, has allergies, or has an autoimmune disease. The (Continued)

method involves analyzing a sample of a body fluid of a transplant candidate or recipient, allergy patient or autoimmune disease sufferer and correlating the relative amounts of each immunoglobulin isotype and subtype, such that the distribution of isotypes and subtypes is an indication of success of the transplant in the candidate and recipient or the prognosis of the autoimmune disease.

20 Claims, 13 Drawing Sheets

Related U.S. Application Data

(60) Provisional application No. 61/167,365, filed on Apr. 7, 2009.

(51) Int. Cl.
G01N 33/564 (2006.01)
G01N 33/68 (2006.01)

(52) U.S. Cl.
CPC ............ *G01N 33/6893* (2013.01); *G01N 2333/70503* (2013.01); *G01N 2333/70539* (2013.01); *G01N 2800/245* (2013.01); *G01N 2800/52* (2013.01)

(58) Field of Classification Search
CPC .......... G01N 2333/70503; G01N 2333/70539; G01N 2800/52; G01N 2800/245
See application file for complete search history.

(56) References Cited

U.S. PATENT DOCUMENTS

| 6,150,122 | A | * | 11/2000 | Lee | .................. | G01N 33/54313 |
| | | | | | | 435/7.1 |
| 7,189,516 | B2 | * | 3/2007 | Mapes | ............. | G01N 33/54313 |
| | | | | | | 435/7.1 |
| 2003/0232397 | A1 | * | 12/2003 | Brown | ............ | G01N 33/54313 |
| | | | | | | 435/7.21 |

OTHER PUBLICATIONS

Arnold et al. IgA1/2 and IgG2/4 isotypes anti-HLA antibodies in sera from patients awaiting kidney re-transplantation. Tissue Antigens 67 (6): 496, (Jun. 2006).*

Villadangos et al. Proteolysis in MHC Class II Antigen Presentation: Who's in Charge. Immunity 12: 233-239 (Mar. 2000).*

Heinemann et al. Immunoglobulin isotype-specific characterization of anti-human leucocyte antigen antibodies eluted from explanted renal allografts. Human Immunology 68: 500, (2007).*

* cited by examiner

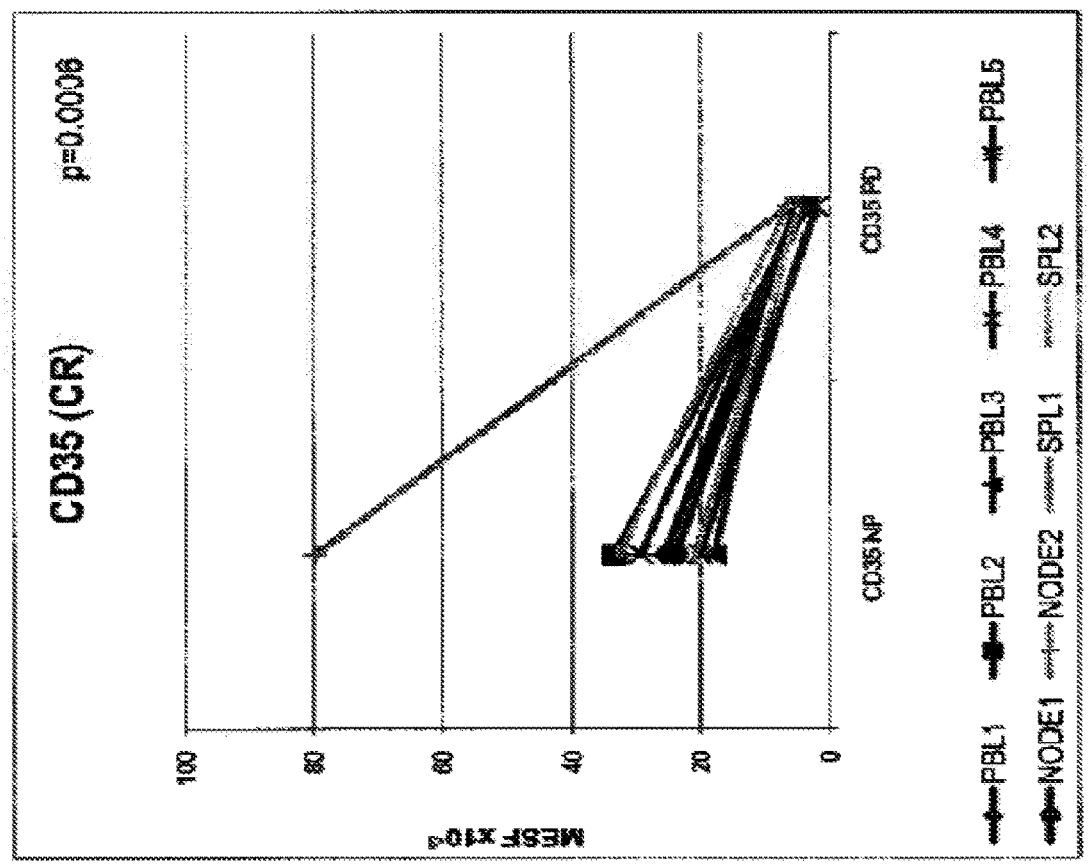
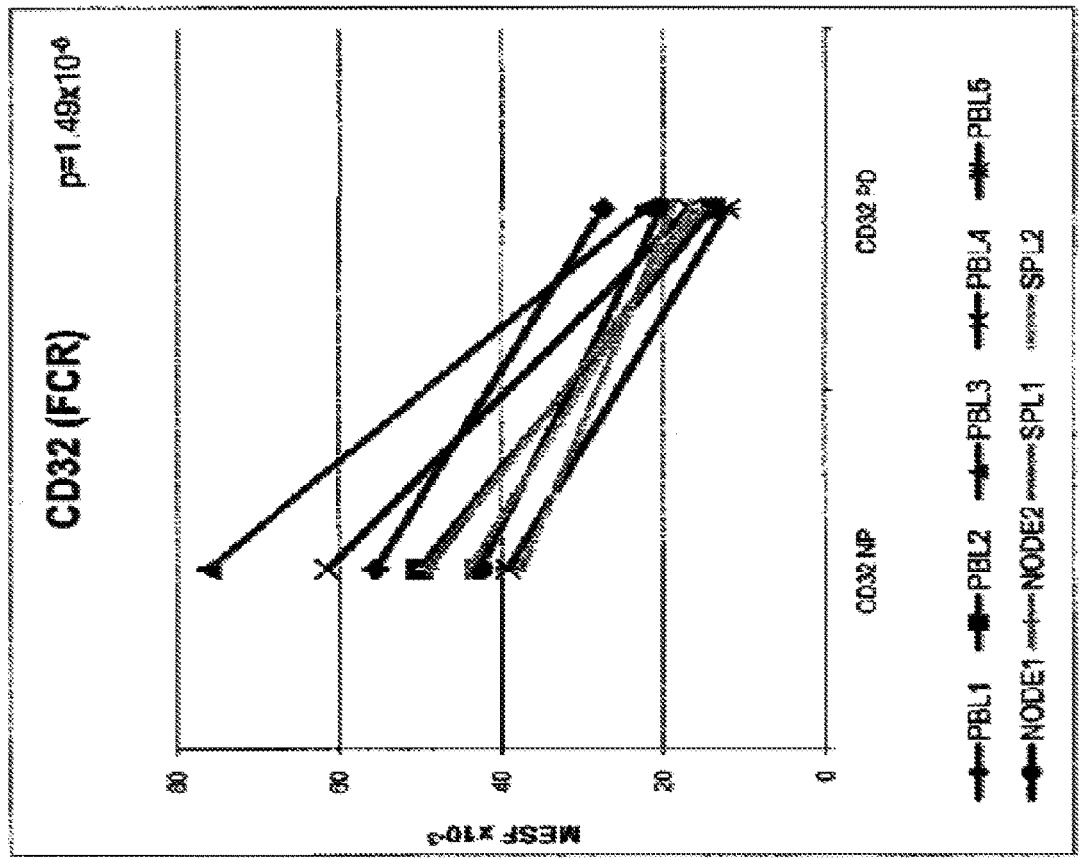
FIG. 9B
FIG. 9A

METHODS AND KITS FOR SCREENING TRANSPLANT RECIPIENTS AND CANDIDATES

RELATED APPLICATION

The present application is a continuation of U.S. non-provisional application Ser. No. 12/755,843, filed Apr. 7, 2010 (issued as U.S. Pat. No. 9,528,988 on Dec. 27, 2016), which is hereby incorporated herein by reference in its entirety and which claims the benefit of U.S. provisional application Ser. No. 61/167,365 filed Apr. 7, 2009 in the U.S. Patent and Trademark Office, which is hereby incorporated herein by reference in its entirety.

TECHNICAL FIELD

This application provides methods and kits to assay a sample of a body fluid or cells to determine amounts of immunoglobulin subclasses and subtypes for antibody having specificity to bind to an antigen found in a major histocompatibility complex protein, to obtain a prognosis or diagnosis of transplantation success or allergy or autoimmune disease.

BACKGROUND

Immunoglobulins are antibodies secreted by plasma and tissue cells that identify and neutralize antigens, which are substances identified as foreign by the immune system. A common type of antibody structure is tetrametric, having two relatively long polypeptide chains, heavy (H) chains and two shorter polypeptide chains, light (L) chains. The Y-shaped structure arms specifically bind antigens (antigen binding fragment, Fab), and tails structure (Fc) binds to receptors on cells. There are five chain classes of immunoglobulins that are identified by different protein structure: gamma (IgG), mu (IgM), epsilon (IgE), alpha (IgA), and delta (IgD).

Human immunoglobulin G, IgG, is the predominant immunoglobulin involved in secondary immune responses. IgG includes four subclasses (IgG1, IgG2, IgG3, IgG4) and although concentrations in serum vary among subjects, in general IgG1 is found in the highest concentration followed by IgG2, and then IgG3 and IgG4 which have about equivalent concentration in serum. The maturation of the subclasses occurs with T helper cell dependence and IgG2 seems to require more help and evolves as stimulation persists.

However the binding of immunoglobulin subtypes and subclasses to antigens and the correlation of amounts of these proteins to prognosis and diagnosis is not well known. There is a need for methods of obtaining a prognosis or a diagnosis in a transplant donor and recipient and recipient candidate, in an allergy patient and in an autoimmune disease patient, by analyzing amounts of immunoglobulin subclasses and subtypes and determining extents of positive and negative outcomes in transplant candidates and recipients, and in the autoimmune disease and allergy patients.

SUMMARY

A feature provided by the invention herein is a method of characterizing a subject to obtain a prognosis or a diagnosis in which the subject is selected from a transplant candidate, a transplant recipient, an autoimmune patient, and an allergy patient, the method including:

analyzing, in a sample of a body fluid from the subject, amounts of antibodies directed to at least one antigen of a major histocompatibility complex (MHC) protein, such that the antibodies are immunoglobulins selected from a plurality of subclasses and isotypes; and, determining amounts of each subclass and isotype, such that a distribution of the amounts within each subclass and isotype in the sample is an indication of the prognosis of transplant suitability or the diagnosis of the allergy or the autoimmune disease.

Accordingly in an embodiment of the method, the antigen is selected from at least one of: HLA class I, HLA class II, and a portion thereof. For example, the HLA class I antigen is selected from at least one of the group of: HLA class I antigen A, HLA class I antigen B, and HLA class I antigen C. In an alternative example, the HLA class II antigen is selected from at least one of the group of: HLA class II antigen DR, HLA class I antigen DP, and HLA class I antigen DQ. In an embodiment of the method, the plurality of antibody subclasses includes: IgG1, IgG2, IgG3, and IgG4. In an alternative or an additional embodiment, the plurality of antibody isotypes includes: IgG, IgM, IgA, IgD and IgE.

An embodiment of the method includes analyzing a control sample from a normal subject for respective amounts of antibodies directed to MHC proteins, and wherein determining further involves comparing amounts of immunoglobulin subclasses and isotypes in the subject to amounts of immunoglobulin subclasses and isotypes in the normal control. The term "normal" control indicates a sample, such as a serum sample, from a subject that is appropriate to the patient sample, for example, for a transplant candidate, the control sample is from a subject not in need of a transplant. For a transplant recipient, the control sample under some circumstances is a pre-transplant sample from the same patient. For an allergy or autoimmune patient, the control is a sample from a non-allergic subject or from a subject not afflicted with the autoimmune disease. Thus in an embodiment of the method, the determining step further includes comparing amounts in the transplant recipient sample to a pre-transplantation control. A related embodiment further includes analyzing a plurality of post-transplantation samples obtained from the recipient at a plurality of time points.

The method includes samples of the body fluid that are selected from an excretion, a secretion, blood, lymph, serum, plasma, cerebrospinal fluid, bile, and amniotic fluids. For example, the body fluid is plasma or serum.

An embodiment of the method involves:

contacting the sample to a mixture of a plurality of types of beads, such that each bead type includes a microsphere containing: an internal dye and an amino acid sequence from an allelic variant of an MHC antigen, autoimmune antigen or allergen antigen, such that the internal dye and the antigen are unique to the bead type;

contacting the mixture successively with: each of a plurality of monoclonal anti-subject immunoglobulin antibodies, such that the monoclonal antibodies specifically bind one of the plurality of immunoglobulin subtypes and subclasses from the sample; and a detectably-labeled antibody capable of specifically binding to the plurality of monoclonal anti-subject antibodies; and, detecting with an optical device amounts of each internal dye associated with each type of bead, and the amounts of the labeled antibody associated with each type of bead, wherein the amount of label associated with each type of bead is an indication of the amount of each subclass and isotype in the sample.

The phrase "single antigen bead" as used herein refers to a type of bead containing a unique antigen. The bead contains multiple copies of this unique antigen.

In general, the subject is a human and the monoclonal anti-subject antibodies are murine anti-human IgG. However it is envisioned that the method is applicable also to a high value animal, for example, a race horse stallion, in need of a transplant or a diagnosis or prognosis of autoimmune disease or allergy, in which case the monoclonal anti-subject antibodies are, for example, murine anti-equine antibodies. Further, embodiments of the detectably-labeled antibody include an anti-murine antibody obtained from at least one selected from the group of: caprine, lapine, equine, canine, feline, bovine, and ovine. The detectable label is selected from colorimetric, fluorescent, radioactive, and affinity tagged.

In an embodiment of the method, the detectably-labeled antibody is an F(ab)$_2$ fragment specific for a subclass or isotype. For example, the label is a phycoerythrin (PE). In an embodiment, the PE is excited by a wavelength of about 530 nm and emits an orange fluorescence at a wavelength of about 575 nm.

In various embodiments of the method, at least one of the plurality of types of beads is a control absent an MHC antigen; alternatively, at least one of the plurality of types of beads is associated with a plurality of amino acid sequences of antigens from at least one MHC protein. For example, the antigen is an amino acid sequence of a protein selected from the group of: HLA class I, HLA class II, and a portion thereof.

In various embodiments the method includes quantitating the beads in a detection chamber in the optical device, and quantitating involves exciting the beads by illuminating with at least two beams of light of different wavelengths. For example, the optical device is a cytometer. In an embodiment, the beams are lasers. For example, exciting the beads involves illuminating with a red wavelength laser of about 635 nm or a green wavelength laser of about 532 nm. The method in a related embodiment further includes comparing amounts of orange fluorescence to respective amounts of red laser absorption and green laser absorption, and thus identifying amounts of at least one of the subclasses and the isotypes, i.e., measuring relative amounts of IgA, IgE, IgG, IgM, compared to each other, or measuring relative amounts of IgG1, IgG2, IgG3 and IgG4 compared to each other, or measuring both sets of amounts.

In an embodiment of the method, analyzing further includes observing a medical outcome in the subject and associating the outcome with comparative amounts of the subclasses and the isotypes, thereby developing a prognostic and diagnostic tool. For example, a surprising finding using the method herein is that a presence of at least one of IgG1 and IgG3 is associated with a poor prognosis or diagnosis, in a transplant patient or a transplant candidate. Further, a presence of at least one of IgG2 and IgG4 is associated with a good prognosis, or a good diagnosis.

An embodiment of the method involves the prognosis or diagnosis of the autoimmune patient and the autoimmune disease is selected from the group of: Hashimoto's thyroiditis; idiopathic myxedema, a severe hypothyroidism; multiple sclerosis, a demyelinating disease marked by patches or hardened tissue in the brain or the spinal cord; myasthenia gravis which is a disease having progressive weakness of muscles caused by autoimmune attack on acetylcholine receptors at neuromuscular junctions; Guillain-Barre syndrome, a polyneuritis; systemic lupus erythematosis; uveitis; autoimmune oophoritis; chronic immune thrombocytopenic purpura; colitis; diabetes; Grave's disease, which is a form of hypothyroidism; psoriasis; pemphigus vulgaris; Duchenne's muscular dystrophy; scleroderma; Sjögren's syndrome; Takayasu's arthritis; phagoneuroglanulomatosis; cirrhosis; Birdshot retinopathy; silicone implant-induced autoimmune reaction; anticoagulant deficiency due to antibodies; and rheumatoid arthritis.

An embodiment of the method of analyzing amounts further includes:

contacting a mixture of a plurality of types of beads with the sample, wherein each bead type includes a microsphere containing: an internal dye, and an amino acid sequence of an allergen, wherein the internal dye and the allergen are unique to the bead type;

contacting the mixture successively with: each of a plurality of monoclonal anti-subject immunoglobulin antibodies, such that the monoclonal antibodies specifically bind at least one of the plurality of immunoglobulin subtypes and subclasses, such that the plurality of isotypes is at least one selected from the group of: IgE, IgG, IgM, IgA, and IgD, such that the plurality of subclasses is at least one selected from the group of: IgG1, IgG2, IgG3, and IgG4; and a detectably-labeled antibody capable of specifically binding to the plurality of monoclonal anti-subject antibodies; and, detecting with an optical device amounts of each of the internal dyes associated with each of the types of beads, and the amounts of the labeled antibody associated with each of the types of beads, such that the amount of label associated with each type of bead is an indication of the amount of each subclass and isotype in the sample, thereby providing diagnosis and prognosis of atopic individuals and their desensitization.

For example, at least one of the plurality of isotypes is IgE. IgE is referred to as "reagenic" because a high amount of IgE is associated with allergic conditions, and IgE located on basophils and mast cells are known to react to allergens resulting in inflammatory responses.

Accordingly, the prognostic and diagnostic methods herein are useful for monitoring courses of desensitization, such as are offered to allergy patients, to produce a state in which the immune system no longer reacts to an allergen or a class of antigens.

A feature of the invention herein provides a kit for characterizing antibodies to major histocompatibility complex subclasses and isotypes in a vertebrate subject, the kit comprising a plurality of types of beads such that each type of bead is associated with: at least one internal dye; and at least one antigen obtained from a plurality of subclasses and isotypes of major histocompatibility complex (MHC) proteins of the subject; the kit further comprising at least one monoclonal anti-subject antibody capable of specifically binding to an IgG of the subject; a detectably-labeled antibody capable of specifically binding to the monoclonal anti-subject antibody; a container; and instructions for use to characterize presence of and to quantitate the antibody subclasses and isotypes. An embodiment of the kit further includes a negative control which is at least one type of bead absent antigen, i.e., an "empty" bead. An embodiment of the kit further includes instructions for samples from humans, and in this embodiment the at least one monoclonal antibody is murine anti-human antibody. In a related embodiment, the detectably-labeled antibody is an anti-murine antibody obtained from at least one immunized animal selected from the group of: caprine, lapine, equine, feline, canine, bovine, and ovine. Further, the detectably-labeled antibody includes a tag selected from the group of colorimetric, fluorescent, radioactive, and affinity labeled. For example, the detectably-labeled antibody includes phycoerythrin.

A feature of the present invention provides a method of prognosing or diagnosing a subject for transplant suitability or diagnosis or prognosis of allergy and autoimmune disease, the method including:

contacting a sample of cells from the subject successively with each of: an enzyme that removes a subset of cell surface proteins for a time sufficient to remove the cell surface proteins; a mixture of a plurality of types of beads, such that each bead type comprises a microsphere containing: an internal dye and an amino acid sequence from the subclass or isotype of an MHC antigen, in which the internal dye and the antigen are unique to the bead type; a plurality of monoclonal anti-subject immunoglobulin antibodies, such that each of the monoclonal antibodies specifically bind to one of the plurality of immunoglobulin subtypes and subclasses from the sample; and, a detectably-labeled antibody capable of specifically binding to the plurality of monoclonal anti-subject antibodies; and, detecting with an optical device amounts of each of the internal dyes associated with each of the types of beads, and the amounts of the labeled antibody associated with each of the types of beads, such that the amount of label associated with each type of bead is an indication of the amount of each subclass and isotype in the sample. For example, the enzyme is a proteolytic enzyme. For example, the proteolytic enzyme is Pronase™. In alternative embodiments, the proteolytic enzyme is selected from at least one of the group of: serine proteinases, cysteine proteinases, aspartic proteinases, and metalloproteinases.

In various embodiments, the at least one monoclonal antibody is a murine-anti human antibody produced by at least one immunized animal selected from the group of: caprine, lapine, equine, feline, canine, bovine, and ovine. In various embodiments, the detectably-labeled antibody is selected from colorimetric, fluorescent, radioactive, and affinity tagged. In general, the optical device is a flow cytometer.

In general, the sample includes at least one cell. For example, the cell is a human cell. Further, the at least one cell includes an antigen from at least one MHC protein selected from the group of: HLA class I, HLA class II, and a portion thereof. For example, the HLA class I antigen is at least one selected from the group of: antigen A, antigen B, and antigen C. For example, the HLA class II antigen is at least one selected from the group of: antigen DR, antigen DP, and antigen DQ. For example, the subclasses are at least one selected from the group of: IgG1, IgG2, IgG3, and IgG4. For example, the isotypes are at least one selected from: IgG, IgM, IgA, IgD and IgE.

BRIEF DESCRIPTION OF THE DRAWINGS

FIG. 7A shows a decrease observed HLA class I proteins on cells digested with Pronase.

FIG. 7B shows a slight increase observed for HLA class II protein on cells digested with Pronase. Data show decreases in amounts of complement receptors CD21 (CR) and CD35 (CR) and for Fc-gamma receptor CD32 (FCR).

FIG. 8A shows amounts of HLA-ABC (HLA class I).

FIG. 8B shows amounts of HLA-DR (HLA class II).

FIG. 9A and FIG. 9B are a set of line graphs showing Fc-gamma receptor CD32 (FCR) and complement receptor CD35 (CR) on the surface of cells that were enzymatically digested using Pronase (PD, data points on right), and on control cells (NP, data points on left) not digested. The samples were cell types peripheral blood lymphocytes (PBL), spleen B lymphocytes (SBL), and node B lymphocytes (NBL).

FIG. 9A shows data obtained for CD32 (FCR) in MESF units.

FIG. 9B shows data obtained for CD35 (CR) in MESF units.

FIGS. 10A and C show three-color flow cytometry crossmatch data for T cell CD55 (DAF) surface protein, digested with Pronase (FIG. 10C), and control cells not digested (FIG. 10A).

FIGS. 10B and D show three-color flow cytometry crossmatch data for B cell CD55 (DAF) surface protein, digested with Pronase (FIG. 10D), and control cells not digested (FIG. 10B).

The digestion clearly shifts the distribution of cells from right quadrants to left quadrants, indicating that CD55 (DAF) was completely removed.

FIG. 11A, FIG. 11B, FIG. 11C and FIG. 11D are a set of three-color flow cytometry crossmatch data of T cells or B cells digested with Pronase, and analyzing amounts of CD59 (protectin) surface protein on the cells.

Figure 11A:
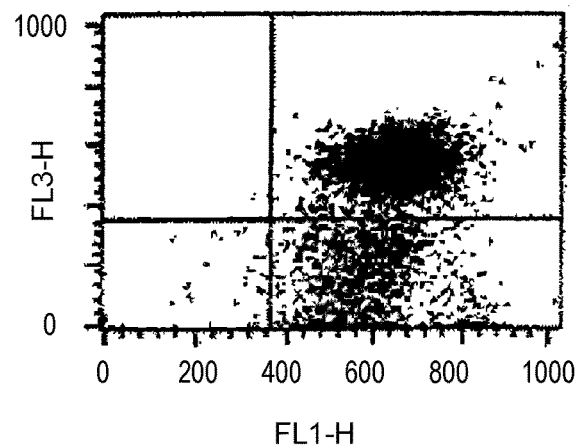

FIGS. 11A and C show three-color flow cytometry crossmatch data for T cells, having a CD59 surface protein, that were digested with Pronase (FIG. 11C), and control cells not digested (FIG. 11A).

Figure 11B:
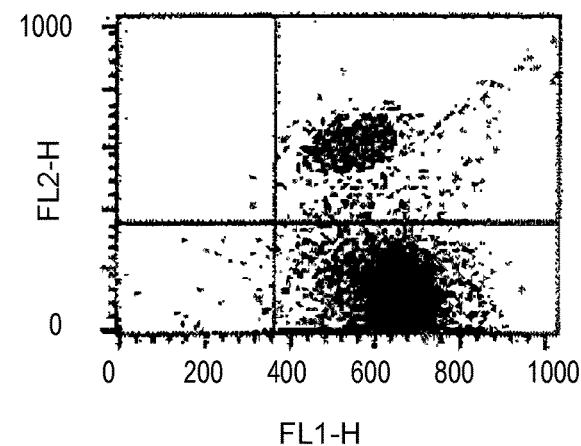
Figure 11C:
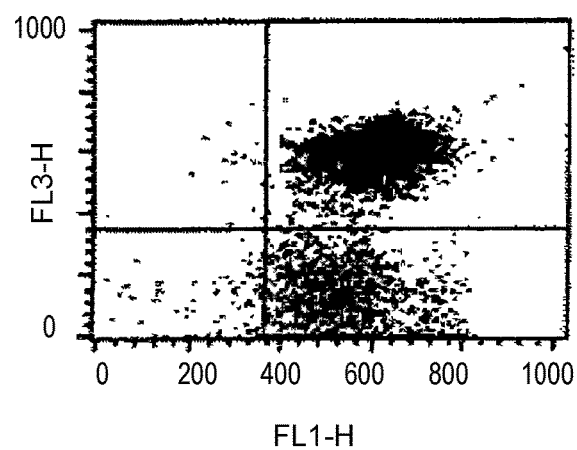
Figure 11D:
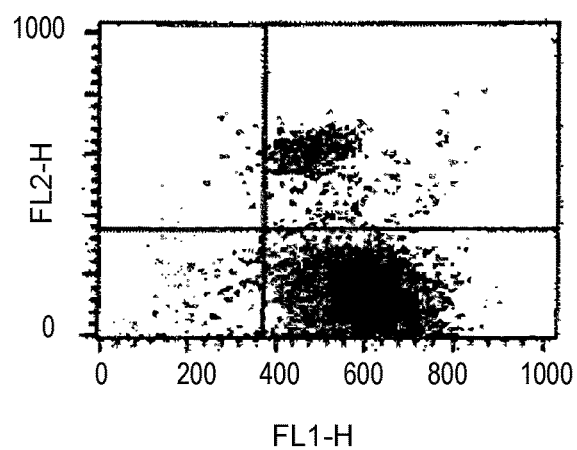

FIGS. 11B and D show three-color flow cytometry crossmatch data for B cells, having a CD59 surface protein, that were digested with Pronase, (FIG. 11D), and control cells not digested (FIG. 11B).

The data show that CD59 (protectin) was partially degraded.

DETAILED DESCRIPTION

Immune responses that are produced by a recipient specific for donor antigens (i.e., "non-self" or "allogeneic") are the primary cause of rejection of the transplanted cells and tissue, and result in graft failure. Strategies for avoiding rejection have focused on minimizing antigenic differences between donor and recipient by matching Human Leukocyte Antigens (HLA; also known as Major Histocompatibility (MHC) antigens) and by subjecting the transplant recipient to potent immunosuppression.

HLA antigens are encoded by a large number of gene loci, each having many allelic alternations, HLA Class I and HLA Class II antigens (e.g., HLA-A, HLA-B, HLA-DR) have been shown to especially affect graft survival. A significant HLA matching effect was observed with HLA-A, B, and DR match in kidney transplantation and graft survival and rejection in pancreas, heart, lung and bone marrow transplantation.

Complement dependent cytotoxic (CDC) cross matching (XM) using human antibodies and HLA on lymphocytes as the target, has been a routine test since it was first described and was shown to define antibodies that result in the hyper-acute rejection of solid organ transplants (Terasaki P. I. et al., 1978 Am J Clin Pathol. 69(2): 103-20). However, only antibodies that produced strong responses could be demonstrated or identified. Subsequent analysis of the test determined that it was extremely insensitive, particularly as xenogeneic rabbit serum was used as a complement source because human serum and autologous serum do not fix complement. Species specific antibodies and complement do not work on targeted lymphocytes because complement inhibitory factors are found associated with cells in serum. Xenogeneic complement also has heterophile antibodies which assist the CDC reaction. Further careful screening of rabbit sera was required because rabbit sera are cytotoxic to human lymphocytes.

Data from CDC XM show that pre-existing antibodies ("alloantibodies") cause the majority of hyper-acute rejections, for example, accelerated acute rejection of a graft within 48 hours of transplant, and acute rejection within days of transplant. Flow cytometry cross match assays (FCXM) were developed as a more sensitive assay for presence of antibodies. However, these tests are associated with problems of poor sensitivity and specificity, including a serious number of a high number of false-positive results. Thus, there remains a long felt need for a method that determines which antibodies fix human complement, and identifies antibodies in vitro to predict a clinical outcome.

Examples herein provide methods that utilize human serum as a complement source and identify immunoglobulin subclasses and isotypes, for example IgG1 and IgG3, that are associated with complement fixation and phagocytosis. Data herein show correlation between specific immunoglobulin subclasses and isotypes and clinical outcome, and provide methods for prognosing or diagnosing for a patient, e.g., a potential transplant recipient, a post-transplant recipient, an allergy patient, and an autoimmune patient.

The basic functions of the complement system are lysis of cells, bacteria and viruses; opsonization which promotes phagocytosis of particulate antigens; binding to specific complement receptors on cells of the immune system triggering specific cell functions, inflammation, and certain immunoregulatory molecules; and immune clearance, which removes immune complexes from immune system and deposits them in the spleen and liver. See Kendrew, J., 1994 "Encyclopedia of Molecular Biology", Blackwell Science Ltd. 218-222.

The proteins and glycoproteins that constitute the complement system are synthesized by liver hepatocytes, and significant amounts are produced also by tissue macrophages, blood monocytes and epithelial cells of the genitourinary tract and gastrointestinal tract. The three pathways generate homologous variants of protease C3-convertase. The classical complement pathway typically requires antibodies for activation (specific immune response), whereas the alternative and mannose-binding lectin pathways are activated by C3 hydrolysis or antigens without the presence of antibodies (non-specific immune response).

In these pathways, a C3-convertase cleaves and activates component C3, producing C3a and C3b and causing a cascade of further cleavage and activation events. C3b binds to the surface of pathogens leading to greater internalization by phagocytic cells by opsonization. C5a is an important chemotactic protein, helping recruit inflammatory cells. Both C3a and C5a have anaphylatoxin activity, directly triggering degranulation of mast cells as well as increasing vascular permeability and smooth muscle contraction. C5b initiates the membrane attack pathway, producing the membrane attack complex (MAC) consisting of C5b, C6, C7, C8, and polymeric. MAC is the cytolytic end product of the complement cascade forming a transmembrane channel and causing osmotic lysis of the target cell. Kupffer cells and other macrophage cell types act to clear complement-coated pathogens. As part of the innate immune system, elements of the complement cascade are ancient, and are found in species earlier than vertebrates, for example, the horseshoe crab.

The classical pathway is triggered by activation of the C1-complex. The complex is formed by two molecules of C1r, and two molecules of C1s to produce C1qr2s2. Triggering, occurs by binding C1q to IgM or IgG complexed with antigens. A single IgM initiates the pathway, or multiple IgG molecules initiate the pathway. Alternatively, C1q binds directly to the surface of the pathogen. Binding results in conformational changes in the C1q molecule, leading to activation of two C1r (a serine protease) molecules that cleave C s, another serine protease. The C1r2s2 component cleaves C4 and then C2, producing C4a, C4b, C2a, and C2b. C4b and C2a bind to form the classical pathway C3-convertase (C4b2a complex), which promotes cleavage of C3 into C3a and C3b. C3b binds to C4b2a (the C3 convertase) to make C5 convertase (C4b2a3b complex). C3-convertase is inhibited by decay accelerating factor (DAF), which is bound to erythrocyte plasma membranes by a glycosylphosphatidylinositol linkage (GPI anchor). Activity of C1r and C1s is controlled by C1-inhibitor.

The alternative pathway is triggered by spontaneous C3 hydrolysis cleavage of the thioester bond by a condensation reaction (C3 is mildly unstable in aqueous environment) to form C3a and C3b. This pathway does not rely on pathogen-binding antibodies as do the classical pathways. C3b covalently binds to a pathogenic membrane surface if appropriately situated with respect to that surface. The C3a and C3b protein fragments are deactivated by rejoining with each other in absence of interacting with a pathogen in the blood. Upon binding to a cellular membrane, C3b binds to factor B to form C3bB. This complex in the presence of factor D is cleaved into Ba and Bb. Bb remains covalently bound to C3b and forms C3bBb which is the alternative pathway C3-convertase. Protein C3 is produced in the liver.

The C3bBb complex binds to the surface of the pathogen, and catalyzes the hydrolysis of C3 in the blood into C3a and C3b, which positively affects the number of C3bBb bound to a pathogen. After hydrolysis of C3, C3b complexes to form C3bBbC3b, which cleaves C5 into C5a and C5b. C5b complex with C6, C7, C8, and C9 (C5b6789) to form the membrane attack complex (MAC), which is inserted into the cell membrane. MAC forms a channel, and initiates cells lysis. C5a and C3a also trigger mast cell degranulation.

Control of the complement pathway is accomplished by partial or total removal of regulators to complement activation (RCA). Cells in the human body are protected by one or more of the membrane-associated regulators of complement activation (RCA) proteins including decay activating factor (DAF), membrane cofactor protein (MCP), protectin (CD59), CD55 and CD46. Factor H and C4BP, for example, circulate in the plasma and are recruited to self-surfaces through binding to host-specific polysaccharides such as the glycosaminoglycans. Factor H and C4BP proteins disrupt the formation of the convertases and shorten the half-life of complexes. Presence of these RAC proteins on self-surfaces, and absence from the surfaces of foreign particles, results in these regulators targeting the complement system to functional locations, for example on the surface of an invading bacterium, and preventing complement activation on host (self) cells or tissues.

C3bBb, an initializing convertase of the alternative pathway, forms upon factor B binding to C3b and is subsequently cleaved. Factor H competes with factor B for binding to C3b. Thus, C3bBb is not formed or is greatly reduced in amount if factor H binds to C3b. Factor H binds with greater affinity to C3b in the presence of sialic acid, a component of most human cells. Thus, presence of sialic acid and the binding of factor H prevent the complement cascade from activating if C3b is bound to a self cell. Alternatively, the complement system cascade functions as intended when factor B binds to C3b on a foreign particle in the absence of sialic acid (Norman D. G. et al., 1991 J Mol Biol 219(4): 717-725; Uhrinova, S. et al., 2003 Proc Natl Acad Sci USA 100(8): 4718-4723; Szakonyi, G. et al., 2001 Science 292(5522): 1725-1728).

The immune system includes the innate and the adaptive immune system. The innate immune system prevents penetration and spread of infectious agents by physical, biochemical and cellular barriers (e.g., skin, mucosa, lysozymes, complement and phagocytes). The adaptive immune system includes cells and molecules, such as T cells and B cells. T cells regulate the immune response and produce cellular immunity, and B cells result in humoral immunity. B cells differentiate into plasma cells after exposure to antigen, and synthesize antibodies or immunoglobulins that are specific to bind to the antigen (Roitt, I. et al., 1996 Immunology, 4 ed. Mosby: London, England; Stitis, D. P. et al., 1990 Basic and Clinical Immunology, 7 ed. Appleton and Lange: Norwalk, Conn.).

The glycoprotein immunoglobulin G (IgG), a major effector molecule of the humoral immune response in man, accounts for about 75% of the total immunoglobulins in plasma of healthy individuals. The immunoglobulins of the other classes or isotypes, IgM, IgA, IgD and IgE, each of which has characteristic properties and functions, constitute the other 25% of the immunoglobulins (Spiegelberg, H. L. 1974 Adv Immunol 19: 259-294). Appearance of specific IgG antibodies generally corresponds with the maturation of the antibody response, which is switched on upon repeated contact with an antigen or allergen. IgG antibodies have a relatively high affinity and persist longer in circulation compared to antibodies of the IgM class. The five classes of human immunoglobulins have characteristic amino acid compositions and sequences. Differences in amino acid sequences are the basis for antigenic differences between these molecules and subsequent immunological recognition by specific antibodies.

Extensive studies with specific polyclonal rabbit antisera that were produced using homogeneous human IgG myeloma proteins as antigens revealed the existence of four distinct subgroups or subclasses of human IgG, which were designated IgG1, IgG2, IgG3 and IgG4, respectively (Grey, H. M. et al., 1964 J Exp Med 120: 253-266; Gergely, J. et al., 1967 Immunochemistry 4: 101-107; World Health Organisation 1996 WHO Technical Series Report number 35,953). Early studies were performed with polyclonal antisera, which were rendered specific by absorption, a costly and time-intensive procedure that results in only small amounts of reagent (Jefferis, R 1986 Monogr Allergy 19: 71-85). Subsequently, monoclonal antibodies specific for human IgG and its subclasses became available, which permitted more reproducible measurements of IgG subclass levels (Reimer, C. B. et al., 1984 Hybridoma, 3: 263-275;

Vlug, A. et al., 1989 Eur Clin Lab 8: 26-35; Schur, P. H. et al., 1987 Ann Allergy 58: 89-99).

Quantitatively, serum concentration of IgG1 is greater than IgG2, which is greater than both IgG3 and IgG4 (Shakib, F. et al., 1980 Ric Clin Lab 10: 561-580; French, M. 1986 Monogr Allergy 19: 100-107). These immunoglobulin subclasses have greater than 95% homology in amino acid sequences of constant domains of the heavy chains. IgG subclasses differ in the amino acid sequences and structure of hinge regions between the Fab arms (Fragment antigen binding) and the two carboxy-terminal domains (CH2 and CH3) of the heavy chains.

The IgG subclasses differ with respect to the number of inter-heavy chain disulfide bonds in the hinge region (Michaelsen, T. E. et al., 1993 Mol. Immunol 30: 35-40). The structural differences between the IgG subclasses result in distinct susceptibilities to proteolytic enzymes, such as papain, plasmin, trypsin, and pepsin.

IgG3 is very susceptible to cleavage by these enzymes, whereas IgG2 is relatively resistant to enzymatic cleavage. IgG1 and IgG4 subclasses exhibit an intermediary sensitivity to enzymatic cleavage compared to IgG3 (highest susceptibility) and IgG2 (lowest susceptibility).

The IgG subclass distribution in specific antibody responses differs for reasons including structure of the antigen (nature of carrier, number and nature of the epitopes, physicochemical properties), dose and route of entry, and genetic constitution of the host. In contrast to T cell-independent (thymus-independent) antigens, T cell-dependent thymus-dependent) antigens include interaction with helper T lymphocytes to stimulate B-lymphocytes to initiate antibody production. Stimulation of antibody responses to certain antigens selectively increases IgG antibodies of certain subclasses (Soderstrom, T. et al., 1985 J Immunol 134: 1-3; Burton, D. R. et al., 1992 Adv Immunol 51: 1-84; Bredius, R. G. M. 1994 thesis "Effector functions of antibacterial IgG subclass antibodies," Amsterdam). However, antibodies specific to bacterial and viral protein antigens such as tetanus toxoid or outer-membrane components, which are T cell-dependent antigens, are detected in all IgG subclasses. IgG antibodies specific to polysaccharide antigens, which are generally T cell-independent, show a much more pronounced subclass distribution. Immunization with encapsulated bacteria leads to an almost exclusive IgG2 anti-polysaccharide response (Siber, G. R. et al., 1990 New Engl J Med 303: 178-182). In children under the age of 2 years to 3 years, anti-polysaccharide antibodies are detected in the IgG1 subclass (Morell, A. et al., 1990 Eur J Immunol 20: 1513-1517).

Repeated long-term antigenic stimulation with T cell-dependent antigens leads to a marked IgG4 antibody response (Aalberse R. C. et al., 1983 J Immunol 130: 722-726). Anti-viral IgG antibodies are highly restricted to IgG1 and IgG3, with IgG3 antibodies appearing first in the course of infection. The IgG subclass distribution of anti-bacterial response is heterogeneous, since bacteria contain many different antigenic epitopes, with considerable variations in protein and carbohydrate structures. T cells and their cytokines exert differential control over the expression of immunoglobulin isotypes (Schultz, C. L. et al., 1991 Curr Opin Immunol. 3: 350-354).

The IgG subclass determination of antigen-specific antibodies remains cumbersome. A drawback is a lack of generally accepted international age-related reference values and a lack of reproducibility in assay results.

Humoral immunity functions through a number of processes including complement fixation and phagocytosis. Complement fixation (CF) occurs following antibody-antigen reaction and involves the chemical activation of a complement, which is a group of proteins present in blood plasma and tissue fluid that aids the body's defenses following an immune response. CF causes lysis in bacteria and renders cells more susceptible to phagocytosis or opsonization. Complement fixation amongst immunoglobulin G from highest to lowest is: IgG3, IgG1, IgG2, and IgG4. Thus, IgG2 in particular exhibits little CF compared to the other immunoglobulins, IgG4 increases 10 fold to 100 fold after 1 year to 2 years of allergy desensitization in successfully desensitized patients. IgG3 has potent CF ability and is found as the primary antibody in erythroblastosis fetalis, a potentially life-threatening blood disorder in a fetus or newborn infant believed to be caused by the maternal immunoglobulins attacking the infant's red blood cells (i.e., an Rh-negative mother making IgG3 subclass antibodies to her Rh-positive fetus). IgG2 antibodies are efficiently recognized by the Fc-gammaRIIa (Fc-gammaRIIa-H131 allele), while IgG1 and IgG3 bind to all the Fc-gamma receptor family, and IgG4 binds FcR. This binding results in phagocytosis whether antibody dependent cellular phagocytosis (ADCC) or opsonization.

By specifically binding antigens, IgG antibodies agglutinate and precipitate antibody-antigen products, aid in phagocytosis by macrophages and other cells, block viral receptors, and stimulate other immune responses such as complement fixation. The ability of immunoglobulin G antibodies to identify a foreign body is in general beneficial, as for example, to identify bacteria or viruses in the body. However in the example of transplants and autoimmune disorders, antibodies result in profound negative effects by activating the immune response against grafts and self tissues. This autoimmune response directed by antibodies results in deleterious complications and even patient deaths. While sensitization most often occurs as a result of pregnancy and prior transplantation, most of the population has been sensitized by infection and allergens which share epitopes with human proteins. Only gnotobiotic animals remain free of sensitization.

An autoimmune disease results when a host's immune response antibodies fail to distinguish foreign antigens from self molecules (autoantigens), eliciting an aberrant immune response. The immune response towards self molecules in an autoimmune disease results from deviation from the normal state of self-tolerance, in which a regulatory mechanism in T cells and B cells capable of reacting against autoantigens is destroyed. This mechanism in autoimmune disorders is prevented by events that occur in the development of the immune system early in life. The cell surface proteins that play a central role in regulation of immune responses by binding and presenting processed peptides to T cells are the major histocompatibility complex (MHC) molecules (Rothbard, J. B. et al., 1991 Annu. Rev. Immunol. 9: 527-565).

The major histocompatibility complex (MHC) is a large cluster of genes on human chromosome 6 that controls many of the activities of the immune cells, including the transplantation rejection process and the killing of virus-infected cells by specific killer T lymphocytes. MHC is part of a larger major immunogenetic complex with many diverse functions. In different mammals, different symbols have been assigned to the MHC, for example, chicken (B), dog (DLA), guinea (GPLA), human (HLA), equine (ELA), mouse (H-2), and rat (RT-1).

Human leukocyte antigens (HLA) are involved in the acceptance or rejection of tissue or organ grafts and transplants. These antigens are found on the surface of most somatic cells, and white blood cells are a standard source of HLA proteins.

The HLA complex antigens are encoded by several loci of about 3,500 kilobase pairs. The portion of the HLA complex includes genes that encode the class I histocompatibility molecules (HLA-A, HLA-B, and HLA-C) and class II histocompatibility molecules (DP, DQ, and DR). Antigenic differences on cells of transplant donors and recipients are the primary cause of rejection of transplanted cells. Prior art strategies for preventing graft rejection rely mainly on minimizing antigenic differences between the donor and the recipient. Thus, the matching of HLA antigens of transplant patients and donors has posed a significant barrier in determining transplant accessibility.

Immunoglobulins are critical in evoking immune responses in transplant recipients to foreign antigens including donor cells and in evoking autoimmune responses. Data herein provide methods to determine amounts of the immunoglobulin subtypes and subclasses in donor and recipient bodily fluids, and to correlate a transplant outcome with the profile of immunoglobulins present in the donor and recipient. The assay is useful also for providing a prognosis and a diagnosis in autoimmune disease patients and allergy patients. The assay developed herein uses microspheres, each type displaying an HLA class I or HLA class II antigen, to accurately and precisely determine the immunoglobulins in a plurality of transplant donor and recipient candidates.

Previous effects of transplantation and other variables in activation of complement by immunoglobulins have been analyzed using a direct assay using beads (Bartel, G. et al., 2007 Transplantation. 83: 727-733). However, this study did not investigate amounts of specific immunoglobulins and the role of immunoglobulin profile in transplant survival.

Microspheres are spherical particles that range in size from one micrometer (micron, μm) to 1000 μm (one mm). Microspheres come in a variety of forms including solid, porous or hollow, plastic, ceramic or glass, coated or uncoated. Glass microspheres are usually between one micrometer to 1000 micrometers in diameter. The term is used also for glass spheres between 100 nanometers to 5 millimeters (mm) in diameter. Hollow glass microspheres, sometimes termed microballoons, have diameters ranging from 10 μm to 300 μm. Microspheres are used in foam, paints, sealers, adhesives, plastics, concrete, and resins. Thus microspheres offer a number of uses because of the many possible ways the surface chemistry of microspheres is manipulated.

Microspheres or beads are commercially available (Luminex Inc.; Austin, Tex.) and are useful, for example, reducing the size of samples needed in testing, yielding more data from one experiment, as multiple functional groups and organic compounds are potentially attached per bead.

Methods and kits herein use microspheres, for example polystyrene microspheres as small as 5.6 μm, that are internally dyed with red and infrared fluorophores. Using different light wavelengths and dyes for different batches of microspheres produces microsphere sets with unique spectra based on the mix of fluorophores used. "Types" of bead are each coated with a reagent specific to a particular assay, so mixtures of types of microspheres capture specific multiple analytes from a sample. Different sets and subsets of types of microspheres are combined to yield an assay, using formats including a microtiter plate or chip, and information is obtained by combining a large number of different sets. These data are obtained using lasers that excite both an internal dye that identifies each microsphere particle, and a reporter molecule (stain, dye, marker etc.). A flow cytometer causes a stream of microspheres to individually pass through a detection chamber. Thus, the cytometer measures each particle as a discrete and unique entity to be measured discreetly. Once in the detection chamber, a red laser excites both the internal red and infrared dyes, for the proper classification of the microsphere set, and a green a laser excites any orange fluorescence associated with binding of the analyte to the microsphere. Since the detection chamber detects both the classification readings and analyte binding readings of each microsphere, the system results in precise and accurate information. Multiple readings are taken for each bead set, further validating the results. In this way, the microspheres described herein are useful for multiplexing of up to 100 unique assays using a single sample, in a rapid and precise assay. The microspheres used herein are applicable for quantitating levels in a sample and for diagnosing or detecting disease states, for example, allergies, Alzheimer's disease, cystic fibrosis, autoimmune disease, cancer, cardiac markers, and amounts of cellular signaling, cytokines, chemokines and growth factors, endocrines, gene expression, microRNA, neurobiology, and pathogens and sequelae physiological changes of infectious diseases.

Histocompatibility reagents and color-coded microspheres and semi-automated laboratory equipment for HLA antigens are commercially available from One Lambda, Canoga Park, Calif. and Genprobe Tepnel Life Sciences, Stamford, Conn.

The methods and kits described herein use buffers to remove unbound or non-specifically bound molecules (e.g., antigens) from the microspheres/beads. Aqueous wash buffers include salts, amino acids, vitamins, and other reagents. McCoy's medium is available from American Type Culture Collection (ATCC), Manassas, Va. catalogue number 30-2007. McCoy's Medium is modified according to the particular testing matrix, for example, different cells types. Methods of washing unbound molecules (e.g., antibodies, enzymes) and reducing non-specific binding include altering the type, pH, and temperature of buffers.

The amount of binding of specific antigens to beads is determined, for example, using fluorescence detection. U.S. Pat. No. 5,948,627 issued Sep. 7, 1999 (Lee et al.) and U.S. Pat. No. 6,514,714 issued Feb. 4, 2003 (Lee et al.) show methods of detecting panel reactive antibodies specific for HLA class I antigens in serum using beads. U.S. Pat. No. 6,150,122 issued Nov. 21, 2000 (Lee et al.) shows kits for determining percentage of PRA in serum, the kit having microbeads coated with HLA antigens, and subsets of microbeads. U.S. Pat. No. 7,189,516 issued Mar. 13, 2007 (Mapes et al.) shows methods of characterizing autoimmune diseases by detecting and measuring analytes using a multiplex assay system.

The examples herein provide methods for screening a sample from a subject, which sample is obtained from a blood or a blood fraction of an organ, or is a cell obtained from tissue. Subjects as used herein include mammals, for example, a human. The subjects are candidate transplant recipients and candidate transplant donors. The subjects to be screened using the methods herein include those in need of transplants including heart, lung, kidney, liver, pancreas, intestine (large and small), cornea, skin, fetal cord blood, peripheral blood mononuclear cells, T lymphocytes and bone marrow.

Methods and kits are provided herein for an assay to determine amounts of immunoglobulins in sera. In one embodiment, the method detects IgG antibody subclasses in human sera ("alloantibodies") 102 that bind to an HLA antigen located on a type of bead 101. Without being limited by any particular theory or mechanism of action, it is here envisioned that IgG2 and IgG4 anti-HLA antibodies in a sample from patient compete for binding in an assay, i.e., are blocking antibodies for certain functions. Examples herein show detecting amounts of these immunoglobulin subclasses and isotypes in patient samples and correlating the amounts and ratios of subclasses and isotypes to either a positive or negative prognosis and a diagnosis.

Data herein show that IgG subclasses have differential complement fixing and phagocytic properties that affect or even determine outcome of a transplant. Methods described herein are performed prior to transplant (pre-transplant) or after (post-transplant).

Examples herein show methods of using human serum as a complement source, the methods involving removing completely or partially cell surface proteins (e.g., DAF, MCP and protectin) using the proteolytic enzyme Pronase (Roche Diagnostic Corp., Indianapolis, Ind.). Pronase was here observed to remove cell surface markers CD21 and CD35 without affecting HLA Class I and HLA Dr. It was observed that CD55 was 95% removed and CD59 was partially removed or degraded. It is envisioned that cell surface complement inhibition markers that are not removed using a proteolytic enzyme are inhibitable using monoclonal or polyclonal $F(ab)_2$ non-complement fixing fragments.

Unless the context otherwise requires, as used in this description and in the following claims, the terms below shall have the meanings as set forth:

The term "subject" as used herein indicates a mammal, for example a human.

The term "patient" as used herein refers to a subject in need of prognosis, diagnosis, or treatment.

The term "transplant" as used herein refers to obtaining a tissue from one location and implanting the tissue at another, for example, from one part of a subject to another location (autologous transplantation), as in the case of a skin graft using the subject's own skin; or from one subject to another (allogenic transplantation), as in the case of transplanting a kidney from a donor to a recipient.

The term "antigen" as used herein refers to a chemical entity capable of provoking an immune response Examples herein show a method of screening a subject to obtain a prognosis or a diagnosis such that the subject is selected from a transplant candidate, a transplant recipient, an autoimmune patient, an allergy patient, and a normal control, the method involving: analyzing in a sample of a body fluid of the subject respective amounts of each of a plurality of antibodies directed to major histocompatibility complex (MHC) proteins, such that the antibodies are immunoglobulin subclasses and isotypes; and, correlating relative amounts of at least two of the immunoglobulin subclasses and isotypes to each other and to amounts in the control, such that a distribution of amounts of the subclasses and isotypes is an indication of the prognosis or diagnosis. In general, the method involves an antigen from a MHC protein that is at least one selected from the group of HLA class I antigen, HLA class II antigen, a portion of the HLA class I antigen and a portion of the HLA class II antigen. For example, the method involves a HLA class I antigen that is at least one selected from the group of: HLA class I antigen A, HLA class I antigen B, and HLA class I antigen C. Alternatively, the method provides a HLA class II antigen that is at least one selected from the group of: HLA class II antigen DR, HLA class I antigen DP, and HLA class I antigen DQ.

In a related embodiment the at least one subtype is a plurality selected from the group of: IgG, IgM, IgA, IgD and IgE. In general, the at least one subclass is a plurality selected from the group of IgG1, IgG2, IgG3, and IgG4. In general, the method provides correlating the relative amounts of the subclasses and isotypes further involving comparing respective amounts of at least two selected from the group of: IgG1, IgG2, IgG3, and IgG4.

In a related embodiment, the method involves an autoimmune patient that is in need of prognosis or diagnosis for a condition selected from the group of Hashimoto's thyroiditis; idiopathic myxedema, a severe hypothyroidism; multiple sclerosis, a demyelinating disease marked by patches or hardened tissue in the brain or the spinal cord; myasthenia gravis which is a disease having progressive weakness of muscles caused by autoimmune attack on acetylcholine receptors at neuromuscular junctions; Guillain-Barre syndrome, a polyneuritis; systemic lupus erythematosis; uveitis; autoimmune oophoritis; chronic immune thrombocytopenic purpura; colitis; diabetes; Grave's disease, which is a form of hypothyroidism; psoriasis; pemphigus vulgaris; Duchenne's muscular dystrophy; scleroderma; Sjögren's syndrome; Takayasu's arthritis; phagoneuroglanulomatosis; cirrhosis; Birdshot retinopathy; silicone implant-induced autoimmune reaction; anticoagulant deficiency due to antibodies; and rheumatoid arthritis (RA).

In yet another embodiment, the method further involves correlating the amounts of the at least one immunoglobulin in a sample taken after transplant to a sample taken before the transplant. In an alternative embodiment, the method further involves correlating the amounts of the at least one immunoglobulin in a plurality of samples taken after transplant.

In general, the method involves a body fluid selected from an excretion, a secretion, or is obtained from blood, lymph, serum, cerebrospinal fluid, bile, and amniotic fluids. For example, the body fluid is plasma or serum.

In yet another embodiment, a method of analyzing the respective amounts further involves: contacting a plurality of types of beads with the sample, such that the beads involve microspheres containing internal dyes that identify each of the types of the plurality, and each type further includes an antigen obtained from the subclass and isotype of the MHC antigen; contacting the beads successively with each of: each of a plurality of monoclonal anti-subject immunoglobulin antibodies, each capable of specifically binding one of the plurality of immunoglobulin subtypes and subclasses from the sample; and a labeled antibody capable of specifically binding to each of the plurality of monoclonal anti-subject antibodies; and, detecting with an optical device amounts of each of the internal dyes associated with each of the types of beads, and the amounts of the labeled antibody associated with each of the types of beads, such that the amount of label associated with each type of bead is an indication of the amount of the subclass and isotype of the MHC antigen in the sample.

In general, the subject is human and the plurality of monoclonal anti-subject antibodies are murine anti-human IgG antibodies. In a related embodiment, the labeled antibody is anti-mouse antibody obtained from at least one animal selected from the group consisting of: caprine, lapine, equine, bovine, and ovine. In general, the labeled antibody is a subtype specific $F(ab)_2$ fragment or a subclass specific $F(ab)_2$ fragment and the label is selected from colorimetric, fluorescent, radioactive, and affinity tagged. For example, the label is alkaline phosphatase, allophycocyanin (APC), biotin, cyanine 5 (Cy5), fluorescein, rhodamine, glucose oxidase, horseradish peroxidase, Peridinin-chlorophyll-protein Complex (PerCP), phycoerythrin (PE) or tandem labels. In a related embodiment, the method involves exciting PE by a wavelength of about 530 nm and emitting fluorescence at a wavelength of about 575 nm (orange).

In a related embodiment, the method involves at least one of the plurality of types of beads is a control absent an MHC antigen. In a related embodiment, at least one of the plurality of types of beads is associated with at least two antigens from one or more MHC proteins. In general, the method involves MHC protein that is selected from the group of the HLA class I antigen, the HLA class II antigen, the portion of the HLA class I antigen and the portion of the HLA class II antigen.

In general, the method involves quantitating the beads in a detection chamber in the optical device and simultaneously or sequentially exciting the beads with at least two beams of light having different wavelengths. In general, the optical device is a cytometer. For example, the cytometer is a Luminex Flow cytometer or another commercially available cytometer. In general, the method involves exciting the beads with at least two beams, such that the beams are lasers. In one embodiment, the laser beam has a wavelength of about 635 nm (red) or about 532 nm (green). In a related embodiment, the method further involves comparing the amount of orange fluorescence to the amount of red laser or green laser absorption, thereby identifying amount of each of the subclasses and isotypes of the MHC protein.

In a related embodiment, correlating further involves observing a medical outcome in the subject and associating the outcome with each of the subclasses and isotypes, thereby developing a prognostic and diagnostic tool for the medical outcome. In a related embodiment, allele DQ5 in a sample is associated with a poor prognosis. In a related embodiment, at least one allele selected from the group Dr18, DQ7 and DQ8 in a sample is associated with a good prognosis.

Another aspect of the examples herein is a kit for screening to obtain a prognosis or a diagnosis in a subject selected from a transplant candidate, a transplant recipient, an autoimmune patient, an allergy patient, and a normal control, the kit including a plurality of types of beads such that each type is associated with at least one internal dye and an antigen of each of a plurality of subclasses and isotypes a major histocompatibility complex (MHC) of the subject, at least one monoclonal anti-subject antibody capable of specifically binding to IgG a subject, a labeled antibody capable of specifically binding to the monoclonal anti-subject antibody, a container, and instructions for use in a sandwich assay that quantitates a plurality of MHC subclasses and isotypes.

In another embodiment, the kit further includes a plurality of types of beads such that each type is associated with particular internal dye and at least one antigen of each of a plurality of subclasses and isotypes a major histocompatibility complex (MHC) of the subject. In another embodiment, the kit includes at least one type of bead absent MHC antigen as a negative control. In another embodiment, the kit includes at least one buffer that is a solution of compounds selected from the classes: salts, amino acids, sugars, proteins, and dyes. For example, the kit includes McCoy's medium or modified McCoy's medium.

In another embodiment, the kit includes instructions for samples from humans, such that the at least one monoclonal antibody is murine anti-human antibody. In another embodiment, the kit includes instructions that describe using a plurality of types of beads having antigens from a plurality of subtypes selected from the group of: IgG, IgA, IgE, IgM, and IgD. In another embodiment, the kit includes instructions that describe using a plurality of types of beads having antigens from a plurality of subclasses selected from the group of: IgG1, IgG2, IgG3, and IgG4.

In general, the labeled antibody is an anti-mouse antibody obtained from at least one immunized animal selected from the group of: caprine, lapine, equine, bovine, and ovine, such that the animal is contacted with mouse antibody. In another embodiment, the labeled antibody is PE labeled goat polyclonal to murine IgG F(ab)2 fragment. In another embodiment, the labeled antibody carries a tag selected from the group of colorimetric, fluorescent, radioactive, and affinity labeled. In general, the labeled antibody is bound to phycoerythrin. In another embodiment, the kit includes an optical device or a portion thereof.

Methods and kits herein use antibodies including isolated and purified antibodies that bind specifically to a target antigen or molecule as defined herein for immunoassay. In certain embodiments, the antibodies of the methods are derived from particular heavy and light chain sequences or comprise particular structural features such as CDR regions comprising particular amino acid sequences. The methods use isolated monoclonal antibodies and various additional compositions containing the antibodies. Methods herein also relate to methods of using the antibodies in vitro to determine amounts of target antigens, thereby facilitating a diagnosis associated with a disorder or condition associated with a poor prognosis or a good prognosis for a graft, transplant, autoimmune disease or allergy.

In order that the present methods may be more readily understood, certain terms are first defined. Additional definitions are set forth throughout the detailed description. The term "immune response" refers to the action of, for example, lymphocytes, antigen presenting cells, phagocytic cells, granulocytes, and soluble macromolecules produced by the above cells or the liver (including antibodies, cytokines, and complement) that results in the production of soluble immunoglobulins.

The term antibody as used to herein includes without limitation whole antibodies and any antigen binding fragment (i.e., "antigen-binding portion") or single chains thereof. A naturally occurring antibody is a glycoprotein comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding portion" of an antibody (or simply "antigen portion"), as used herein, refers to full length or one or more fragments of an antibody that retain the ability to specifically bind to an antigen (e.g., the target immunoglobulin subclasses and isotypes defined herein that are assayed for a prognosis and diagnosis of a subject). The antigen-binding function of an antibody is performed a full-length antibody or by a fragment thereof. Examples of binding fragments encompassed within the term "antigen-binding portion" of an antibody include a Fab fragment, a monovalent fragment comprising the $V_L$, $V_H$, $C_L$ and $C_H$ domains; a F(ab)$_2$ fragment, a bivalent fragment comprising two Fab fragments linked by a disulfide bridge at the hinge region; a Fd fragment comprising the $V_H$ and CH1 domains; a Fv fragment comprising the $V_L$ and $V_H$ domains of a single arm of an antibody; a dAb fragment (Ward, E. S. et al., 1989 Nature 341: 544-546), which consists of a $V_H$ domain; and an isolated complementarity determining region (CDR).

Furthermore, although the two domains of the Fv fragment, $V_L$ and $V_H$, are encoded by separate genes, they can be joined using recombinant methods, by a synthetic linker that enables them to be made as a single protein chain in which the $V_L$ and $V_H$ regions pair to form monovalent molecules (known as single chain Fv (scFv); see e.g., Bird et al., 1988 Science 242: 423-426; and Huston et al., 1988 Proc. Natl. Acad. Sci. 85: 5879-5883). Such single chain antibodies are also encompassed within the term "antigen-binding portion" of an antibody. These antibody fragments are obtained using conventional techniques known to those of skill in the art, and the fragments are screened for utility in the same manner as are intact antibodies.

An "isolated antibody", as used herein, refers to an antibody that is substantially free of other antibodies having different antigenic specificities (e.g., an isolated antibody that specifically binds a target immunoglobulin is substantially free of antibodies that specifically bind antigens other than this immunoglobulin). An isolated antibody that specifically binds a target may, however, have cross-reactivity to other antigens, such as target molecules having the same or similar amino acid sequences. Moreover, an isolated antibody may be substantially free of other cellular material and chemicals.

The terms "monoclonal antibody" or "monoclonal antibody composition" as used herein refer to a preparation of antibody molecules of single molecular composition. A monoclonal antibody composition displays a single binding specificity and affinity for a particular epitope. The monoclonal antibody contains antibody protein molecules that are substantially identical in amino acid sequence and share a single binding specificity and affinity. In a human monoclonal antibody, the protein molecules having variable regions in which both the framework and CDR regions are derived from human sequences. In one embodiment, the monoclonal antibodies are produced by a hybridoma that includes a B cell obtained from a transgenic nonhuman animal, e.g., a transgenic mouse, having a genome comprising a human heavy chain transgene and a light chain transgene fused to an immortalized cell.

As used herein, "isotype" refers to the antibody class (e.g., IgM, IgE, IgG such as IgG1 or IgG4) that is provided by the heavy chain constant region genes. IgE is an important cause of allergy. Allergic sensitization patients develop high amounts of IgG4. Transplant recipients are sensitized even prior to transplantation primarily as a result of pregnancy, and the antibodies are typically IgG and IgM. Sensitization also results from exposure to bacteria, viruses, fungi and allergens. However most sensitization (about 99%) of individuals results from prior transplantation and pregnancies.

The phrases "an antibody recognizing" a target and "an antibody specific for" a target are used interchangeably herein and are synonymous with the commonly used phrase, "an antibody against".

As used herein, the term "affinity" refers to the strength of interaction between antibody and antigen at single antigenic sites. Within each antigenic site, the variable region of the antibody "arm" interacts through weak non-covalent forces with antigen at numerous sites; the more interactions, the stronger the affinity.

As used herein, the term "avidity" refers to an informative measure of the overall stability or strength of the antibody-antigen complex. It is controlled by three major factors: antibody epitope affinity; the valence of both the antigen and antibody; and the structural arrangement of the interacting parts. Ultimately these factors define the specificity of the antibody, that is, the likelihood that the particular antibody is binding to a precise antigen epitope.

A "blocking antibody", as used herein, refers to an antibody that binds to an antigen or molecule and prevents other antibodies from binding to the antigen or molecule.

Standard assays to evaluate the binding ability of the antibodies toward target xenobiotics are known in the art, including for example, ELISAs, western blots and radio-immune assays (RIAs). The binding kinetics (e.g., binding affinity) of the antibodies can be assessed by standard assays known in the art, such as by Biacore analysis.

Monoclonal antibodies (mAbs) can be produced by a variety of techniques, including conventional monoclonal antibody methodology e.g., the standard somatic cell hybridization technique of Kohler and Milstein, 1975 Nature 256: 495. Many techniques for producing monoclonal antibody can be employed e.g., viral or oncogenic transformation of B lymphocytes. Monoclonal antibodies are also commercially available.

An animal system for preparing hybridomas is exemplified by the murine system, and hybridoma production in the mouse system is a well-established procedure. Immunization protocols and techniques for isolation of immunized splenocytes for fusion are known in the art. Fusion partners (e.g., murine myeloma cells) and fusion procedures are also known.

In certain embodiments, the antibodies of the methods are monoclonal antibodies.

Such monoclonal antibodies specific to one or more target xenobiotics are generated using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice."

Monoclonal antibodies of the methods can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885, 793; 6,521,404; 6,544,731; 6,555,313; 6,582,915 and 6,593, 081 to Griffiths et al.

Monoclonal antibodies can also be prepared using SCID mice into which human immune cells have been used to reconstitute and immune system, such that a human antibody response can be generated upon immunization of the mice. Such mice are described in, for example, U.S. Pat. Nos. 5,476,996 and 5,698,767 to Wilson et al.

The methods and kits now having been described are exemplified by the following examples and claims, which are exemplary only and are not intended to be construed as further limiting. The contents of all of the references cited are hereby incorporated herein by reference.

EXAMPLES

Example 1. Method of Using an Assay for IgG Subclass Identification

Figure 1:
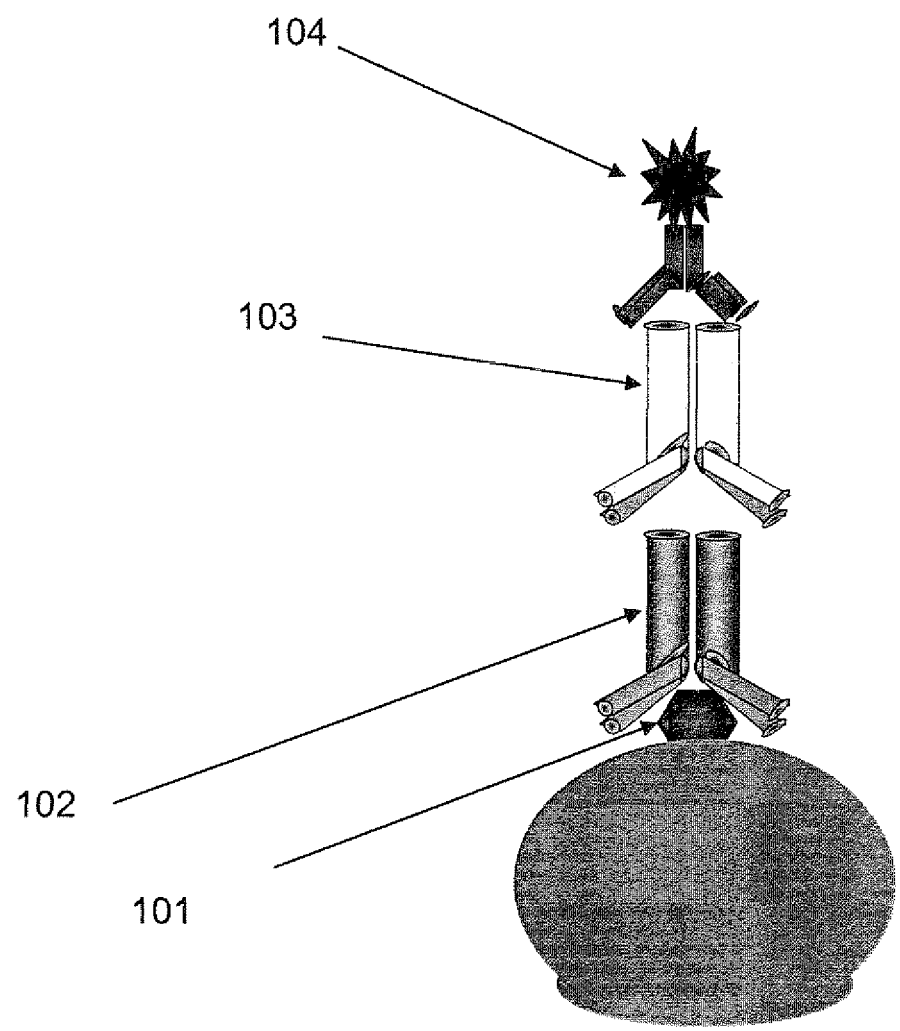
FIG. 1 is a schematic drawing showing components of a method herein. A bead containing a single HLA antigen 101 is contacted to a sample of human serum. The human serum contains an antibody 102 that specifically binds to the HLA antigen. The bead complexed with the antibody is contacted to a murine monoclonal anti-human antibody 103 reagent that specifically binds to an IgG subclass or isotype. Phycoerythrin (PE) labeled goat anti-murine IgG F(ab)$_2$ 104 is added. The method includes three washes with McCoy's medium after each of the steps. For simplicity only one copy of the antigen is shown as a hexagon, however a plurality or even hundreds or thousands of copies are displayed.

To determine IgG subclass components and to quantitate the amounts, HLA unique antigen beads FIG. 1, 101 (available in kits from One Lambda Inc. and Genprobe Tepnel Life Sciences) were incubated with human sera 102 for 30 minutes at 37° C. The beads were washed three times with McCoy's medium (Fisher Scientific; Santa Clara, Calif.), and were incubated with murine monoclonal isotype specific antibody or murine monoclonal human subclass specific antibody 103, then incubated for 30 minutes at 37° C. The beads were again washed three times with McCoy's medium and were incubated with a phycoerythrin (PE) labeled goat anti-murine IgG specific $F(ab)_2$ fragment (Millipore) or PE labeled goat anti-murine isotype specific $F(ab)_2$ fragment 104 (Millipore) respectively. The beads were then detected and quantitated using a Luminex flow cytometer.

Figure 2:
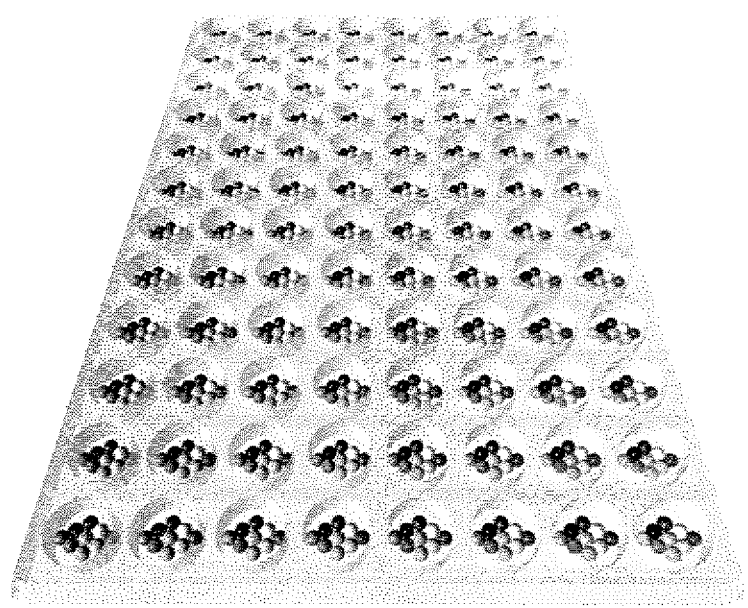
FIG. 2 is a drawing of a bead tray. Each well contains a plurality of different types of single antigen Luminex beads, each type having a single HLA antigen. The bead trays are commercially available from One Lambda (Canoga Park, Calif.) and Genprobe Tepnel Life Sciences (Stamford, Conn.).
Figure 3:
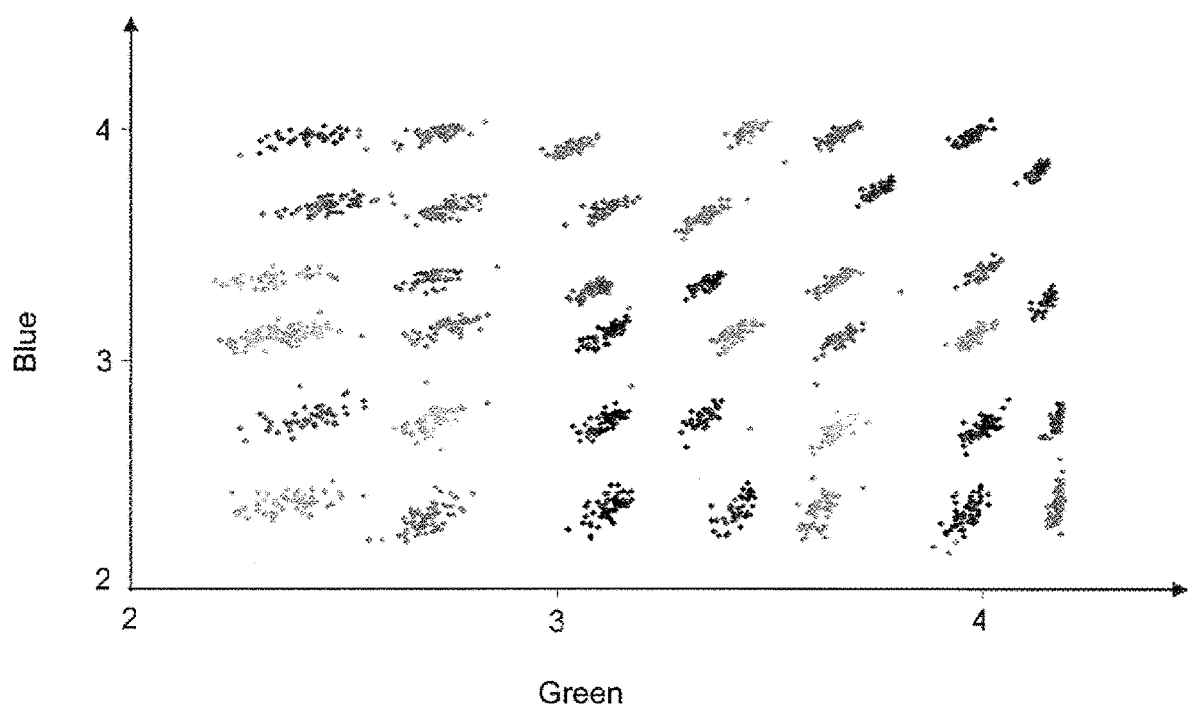
FIG. 3 is a bead map for a two color (blue on the ordinate and green on the abscissa) combination staining using single antigen Luminex beads, each of the types having a spectral signature and bearing a different HLA antigen.

Antibodies that bind IgG specific $F(ab)_2$ fragment and that bind murine isotype specific $F(ab)_2$ fragment 103 were titrated to assure maximum binding and minimal background. Positive control (PC) beads having a number of unique antigens or negative control (NC) beads having no antigens were also tested. PE fluorescence intensity for the beads was measured using a Luminex flow cytometer. The beads were arranged in a Luminex bead tray system, in which each single type of antigen Luminex bead contains a unique HLA antigen (FIG. 2). A bead map for two-color combination staining, in which each type of bead has a spectral signature and each type contains a unique amino acid sequence of an HLA antigen, the different bead types having different antigens, was also obtained (FIG. 3). Each bead 101 passed through the Luminex flow cytometer, and PE fluorescence intensity was measured and the results indicated a total amount of a specific HLA bead that bound to a specific human serum IgG 102. See FIG. 3.

The method and system shown used a single detection reagent, goat anti mouse antibody to detect and to quantitate each of the plurality of mouse monoclonal antibodies specific for each of the IgG subclasses or antibody subtypes in the serum. Improved sensitivity was obtained because the initial signal from the specific binding of the alloantibody to the HLA antigen was detected over a larger range than observed in previous methods, because the signal in this method is amplified by binding detectably-labeled reagent molecules.

Example 2. IgG Subclass Identification of Human Serum Using HLA Class I Antigens Methods were tested for determining amounts of IgG subclasses in ten sensitized human serum samples using HLA class I antigen beads. The subclass binding was tested by extent of fluorescence detected by a cytometer and the results are expressed in raw data units (RDU) of fluorescent intensity.

Bead types each having one of the HLA antigens A23, A24, A25, A32, B27, B37, B38, B57, B58, and B59, available from One Lambda, Inc. and Genprobe Tepnel Life Sciences, were mixed with a sample from a sensitized transplant recipient candidate serum in a Luminex bead tray system for 30 minutes at 37° C. and then washed three times with McCoy's medium. The beads were then mixed with murine monoclonal human subclass specific antibody, and then incubated for 30 minutes at 37° C. The beads were washed three times with McCoy's medium, and were contacted with phycoerythrin (PE) labeled goat anti-murine IgG specific $F(ab)_2$ fragment antibody (Millipore). PE fluorescence intensity for the beads was measured using a Luminex flow cytometer (FIG. 4).

Figure 4:
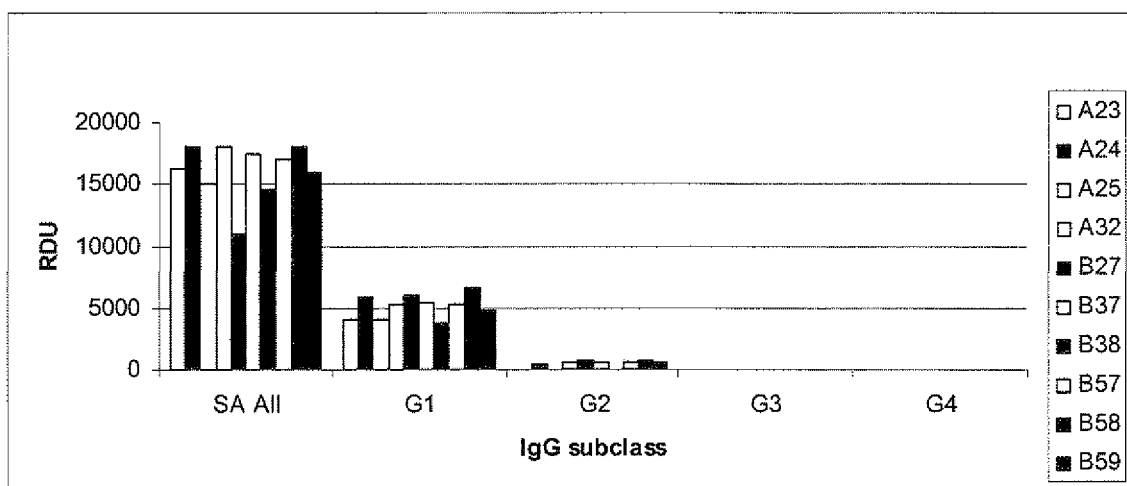
FIG. 4 is a bar graph showing amounts in raw data units (RDU, ordinate) of IgG subclasses (abscissa) in serum from a sensitized transplant candidate. The height of the bars indicates amount of immunoglobulin subclasses (IgG1, IgG2, IgG3, and IgG4) in RDU observed arranged in order indicated along the abscissa for a serum sample that was contacted to a plurality of bead types, each type displaying a single HLA antigen on the bead surface, and a control bead having all HLA subclass surface antigens (SA), analyzed by flow cytometer. The IgG subclasses are distinguished as shown in FIG. 1 by the murine monoclonal antibodies 103. The HLA antigens displayed on the bead types are in order of bars from left to right: HLA-A23 (A23), HLA-A24 (A24), HLA-A25 (A25), HLA-A32 (A32), HLA-B27 (B27), HLA-B37 (B37), HLA-B38 (B38), HLA-B57 (B57), HLA-B58 (B58) and HLA-B59 (B59).

The data show that specific IgG antibodies in the sensitized transplant recipient candidate serum bound preferentially to beads having HLA class I and were detected (FIG. 4). It was observed from the data that primarily IgG1 and IgG2 had bound to the HLA class I beads. Most of the immunoglobulin identified was IgG1 compared to IgG2 and other subclasses. Positive control beads having multiple HLA single antigens were observed to have average RDU values of 13400, 6300, 500, and 1700 for IgG1, IgG2, IgG3 and IgG4, respectively. Negative control beads having no antigen were observed to have average RDU values of 395, 101, 21, and 28 for IgG1, IgG2, IgG3 and IgG4, respectively.

These data demonstrate successful quantitative analysis of samples for IgG subclasses using HLA class I antigen beads to test serum from a sensitized transplant recipient candidate.

Example 3. IgG Subclass Identification of a Sensitized Human Serum Using HLA-DR and HLA-Antigens Methods were tested for determining the IgG subclasses in a sensitized human serum using HLA-DR and HLA-DQ antigen beads. The amount of subclass binding was determined by extent of fluorescence bound to beads, detected by a cytometer.

Beads displaying one of an HLA-DR or an HLA-DQ unique antigen (HLA-DR18, HLA-DQ4, HLA-DQ5, HLA-DQ6, HLA-DQ7 and HLA-DQ8), commercially available from One Lambda Inc. and Genprobe Tepnel Life Sciences) were mixed with a sample of serum from a sensitized transplant recipient candidate in a Luminex bead tray system for 30 minutes at 37° C. Beads were then washed three times with McCoy's medium and were mixed with murine monoclonal anti-human subclass specific antibody, then incubated for 30 minutes at 37° C., washed three times with McCoy's medium, and were contacted with phycoerythrin (PE) labeled goat anti-murine IgG specific $F(ab)_2$ fragment antibody (Millipore). PE fluorescence intensity of the beads was measured using a Luminex flow cytometer. See FIG. 5.

Figure 5:
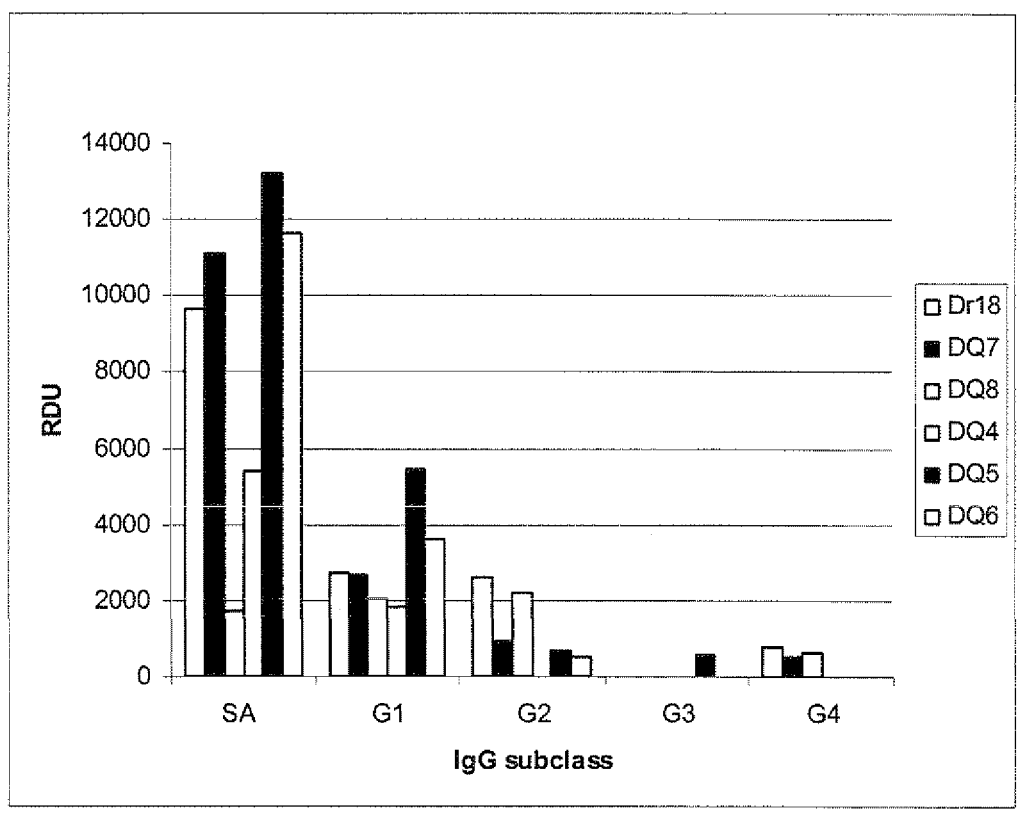
FIG. 5 is a bar graph showing amounts (RDU, raw data units, ordinate) of IgG subclasses arranged in order by HLA allele along the abscissa in serum from a sensitized transplant candidate. Immunoglobulin amounts (IgG1, IgG2, IgG3, and IgG4) were determined in a serum sample by contacting to bead types, each bead type displaying a unique HLA antigen on the bead surface. A control serum sample was contacted also to beads having all HLA subclass surface antigens (SA), and beads were analyzed as shown in FIG. 1. Amounts were determined using a flow cytometer. The height of the bar indicates an amount of IgG in each subclass for each antigen displayed in the following order from top to bottom: HLA-DR18 (Dr18), HLA-DQ7 (DQ7), HLA-DQ8 (DQ8), and HLA-DQ4 (DQ4), HLA-DQ5 (DQ5), and HLA-DQ6 (DQ6).

It was observed that IgG antibodies of specific subclasses in the sensitized transplant recipient candidate serum preferentially bound to HLA-DR and HLA-DQ beads and were detected (FIG. 5). The data show that IgG was the predominant binding component among the IgG subclasses analyzed. One allelic HLA protein antigen, DQ5, detected substantial amounts of IgG2 and IgG3. Substantial IgG4 was detected bound to beads displaying each of the HLA antigens DR18, DQ7, and DQ8.

These data show that the method herein of using HLA-DR and HLA-DQ antigen-displaying beads to bind to antibodies in patient samples and to quantitate immunoglobulin G subclass antibodies was effective, and that reliable data were obtained.

Example 4. Detection of IgG Subclasses in Patients Using Beads Bound to Antigens Human bodily fluid samples from a plurality of transplant candidates, transplant recipients, autoimmune patients, allergy patients, and normal patients are collected. The samples are incubated at 37° C. for 30 minutes with a plurality of types of beads containing the internal dyes that identify each specific type of bead that presents an MHC antigen. The internal dyes identify each specific bead type and MHC antigen, and control beads that contain no antigen. Beads are incubated with samples to bind to those analyze and quantitate IgG antibodies specific to the MHC antigens contained in each type of bead. The beads are then washed three times with McCoy's medium as described above.

The beads are incubated with monoclonal anti-human IgG antibodies capable of specifically binding to each of the types of immunoglobulin subclasses (i.e., IgG1, IgG2, IgG3, and IgG4). The beads are then washed three times with McCoy's medium and are incubated with a PE containing anti-monoclonal antibody that binds specifically to the monoclonal anti-human IgG antibody. Amount of binding is optically detected for each of the internal dyes associated with each of the types of beads, and the amounts of the labeled antibody associated with each of the types of beads is recorded. The amount of fluorescence of the phycoerythrin anti-monoclonal antibody is detected, thereby quantitating the subclasses and isotypes of the antibodies in the samples.

Example 5. Analysis of IgG Subclass Identifications and Patient Prognosis and Diagnosis The methods shown herein for identifying and quantifying immunoglobulin subtypes with the specific bead types were used to monitor a transplant patient. The patient was monitored as a function of time of four months, commencing prior to transplant, and followed post-transplant. Correlation of amounts of IgG antibodies in the samples and prognosis or diagnosis were determined.

The IgG2 subclass of IgG poorly executes (CF) functions as a blocking antibody. Thus a switch to producing IgG2 antibodies in a subject resulted in a lessening of the humoral response compared to strong CF and phagocytic effects of IgG1 and IgG3.

IgG3 is the most efficient immunoglobulin for functioning of human CF. Therefore a presence of IgG3 antibodies was here found to be particularly important as a clinical indicator of negative or only limited success of a transplant in the candidate or recipient, i.e., a presence of IgG3 is here characterized as a "bad" subclass. In contrast, IgG2 and IgG4 antibodies were not associated with human CF and a presence of these subclasses is shown here to be a clinical indicator or prognosis of a positive or successful outcome of a transplant in the candidate or recipient, i.e., IgG2 and IgG4 are "good" subclasses.

Thus, human IgG subclasses were here assayed and correlations provided for clinical indicators as a function of time after transplant. These characterizations are of vital importance due to shortage of matched organs deemed suitable by medical criteria. Descriptions of national exchange of renal organs are provided by the United Network for Organ Sharing (UNOS), which oversees the national database of clinical transplant information and operates the computerized organ sharing system, matching donated organs to recipients. In spite of UNOS efforts, the typical transplant patient experiences a very long wait for an organ.

Example 6. IgG Subclass Analysis of Donor Specific Antibodies (DSA) in Renal Transplant Recipients A single center analysis of 33 renal transplant recipients (RTR) was performed, and patients were observed to be positive for donor specific antibodies (DSA). Further, 80% of the patients were observed by biopsy analysis to be negative for C4d deposition. Thus, most patients were DSA positive and C4d negative.

Patients are routinely tested for DSA, however that analysis includes measuring only IgG content. IgG3 is associated with greatest CF and strength of phagocytosis, followed by IgG1, IgG2, and IgG4 which has the least or no fixation strength and strength of phagocytosis. The IgG4 subclass is a blocking antibody that is increased 10 fold to 100 fold by successful allergic desensitization.

To analyze patient DSA levels for associations with CF and humoral immunity correlation with phagocytosis, four DSA positive RTR sera were analyzed for DSA and IgG subclass by the methods herein.

A Luminex bead assay was performed, using bead types having internal dyes and displayed MHC antigens, McCoy's medium, murine monoclonal antibodies specific for the IgG subclasses and isotypes, and a phycoerythrin labeled goat anti-murine $F(ab)_2$. Software was used to interpret binding and normalized fluorescence intensity as supplied by One Lambda.

TABLE 1

DSA and IgG subclasses in RTR sera (RDU values)

| RTR serum | DSA | IgG1 | IgG2 | IgG3 | IgG4 |
|---|---|---|---|---|---|
| p2336tv | A24 (5000), B45 (8000), DQ5 (3000) | A24 (1000) | A24 (1000), B45 (2000) | — | A24 (800), B45 (700) |
| p23740ar | A1 (5000), B27 (3000), B35 (3000), C4 (1700), DQ6 (1200) | A1 (900), C4 (800), DQ6 (500) | C4 (700) | B35 (550), DQ^ (1000) | — |
| p2374aim | B18 (7000), DQ5 (5000) | DQ5 (1700) | — | — | DQ5 (1000) |
| p2375vdl | A1 (4000), DQ6 (3000) | DQ6 (600) | DQ6 (1000) | — | — |

Data in Table 1 show IgG subclasses and DSA binding to HLA class I and class II alleles, with RDU calculated for each of the DSA and IgG subclasses. It was observed that DSA production was found for a number of alleles. However, the DSA was distributed among the IgG subclasses. IgG2 and IgG4 subclasses were strongly represented among subjects producing DSA. Thus, it is envisioned that these IgG subclasses predict positive DSA results.

Examples herein show methods to determine probabilities that patients have positive DSA results and negative C4d results. Data herein identify the immunoglobulin subclasses most likely to produce a DSA response.

Example 7. IgG Subclass Analysis of DSA in Heart Transplant Recipients

To further identity correlations among IgG subclasses, DSA production, and transplant outcomes, examples herein analyzed pre- and post-transplant transplant samples in heart transplant recipients (HRTX) who were DSA positive.

Of the 33 RTR patients described herein, a significant number were DSA positive and Cd4 negative, about 20% to 50% were determined to be positive for DSA and negative for C4d by biopsy date. Furthermore, many DSA positive patients showed no clinical signs of rejection.

Sera were obtained from one renal transplant recipient candidate sampled at approximately one year intervals: serum V2755, panel A; serum V15809, panel B; and serum V2913, panel C. Serum samples were tested using the methods herein with beads having surface displayed HLA class I antigens. See Table 2 and FIG. 6. Data obtained show that serum V2755 contained a greater amount of IgG3 than IgG1, IgG2 and IgG4; sera V15809 and V29613 produced greater amounts of IgG1 than IgG2 and IgG4.

Figure 6A:
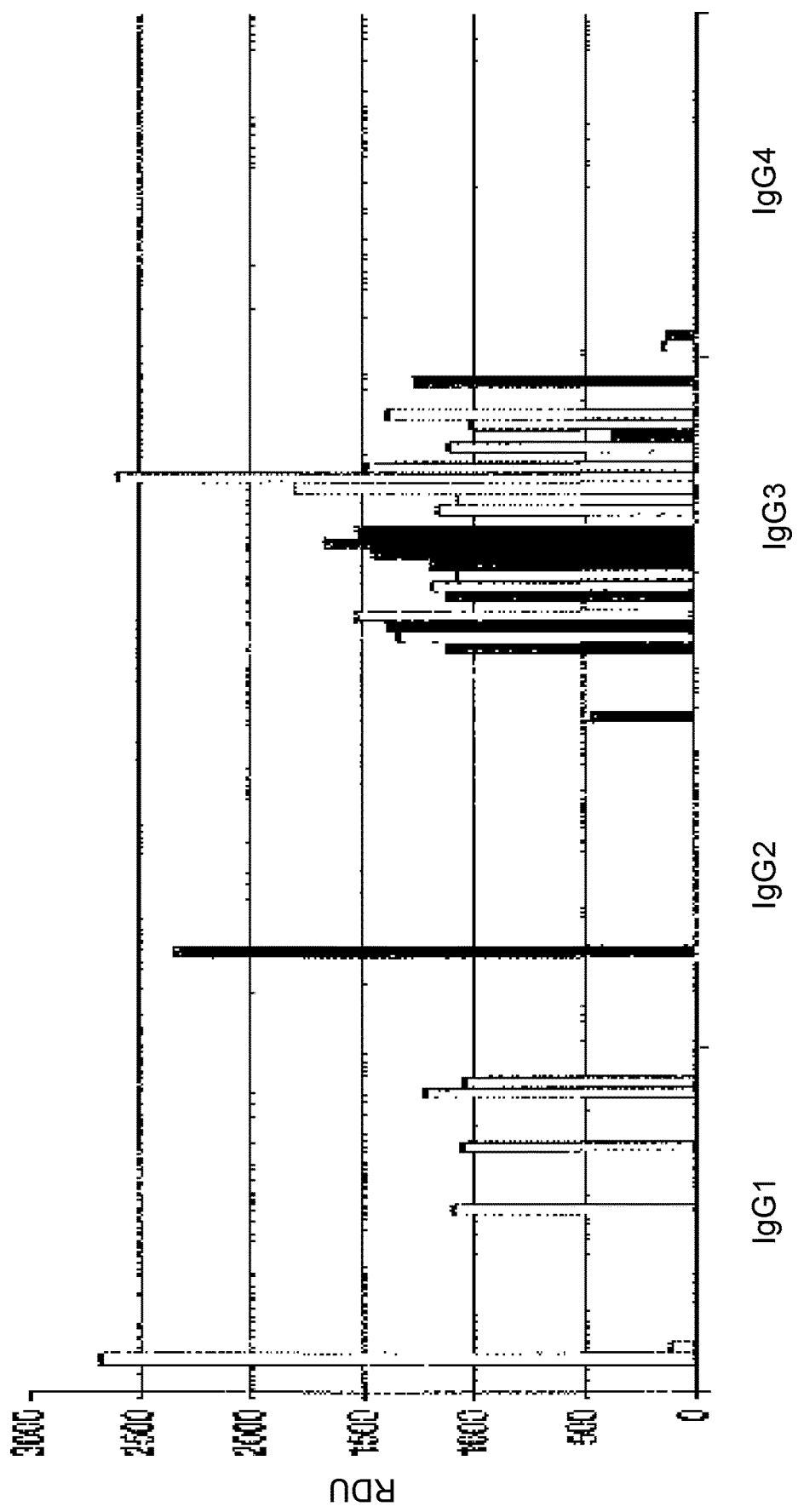
FIG. 6A, FIG. 6B and FIG. 6C are a set of bar graphs showing amounts in RDU, ordinate, of IgG subclasses (arranged along the abscissa) in sera obtained from one renal transplant recipient candidate sampled at approximately one year intervals: serum V2755, panel of FIG. 6A; serum V15809, panel of FIG. 6B; and serum V2913, panel of FIG. 6C. The HLA antigens and amounts of each are shown in Table 2.
Figure 6B:
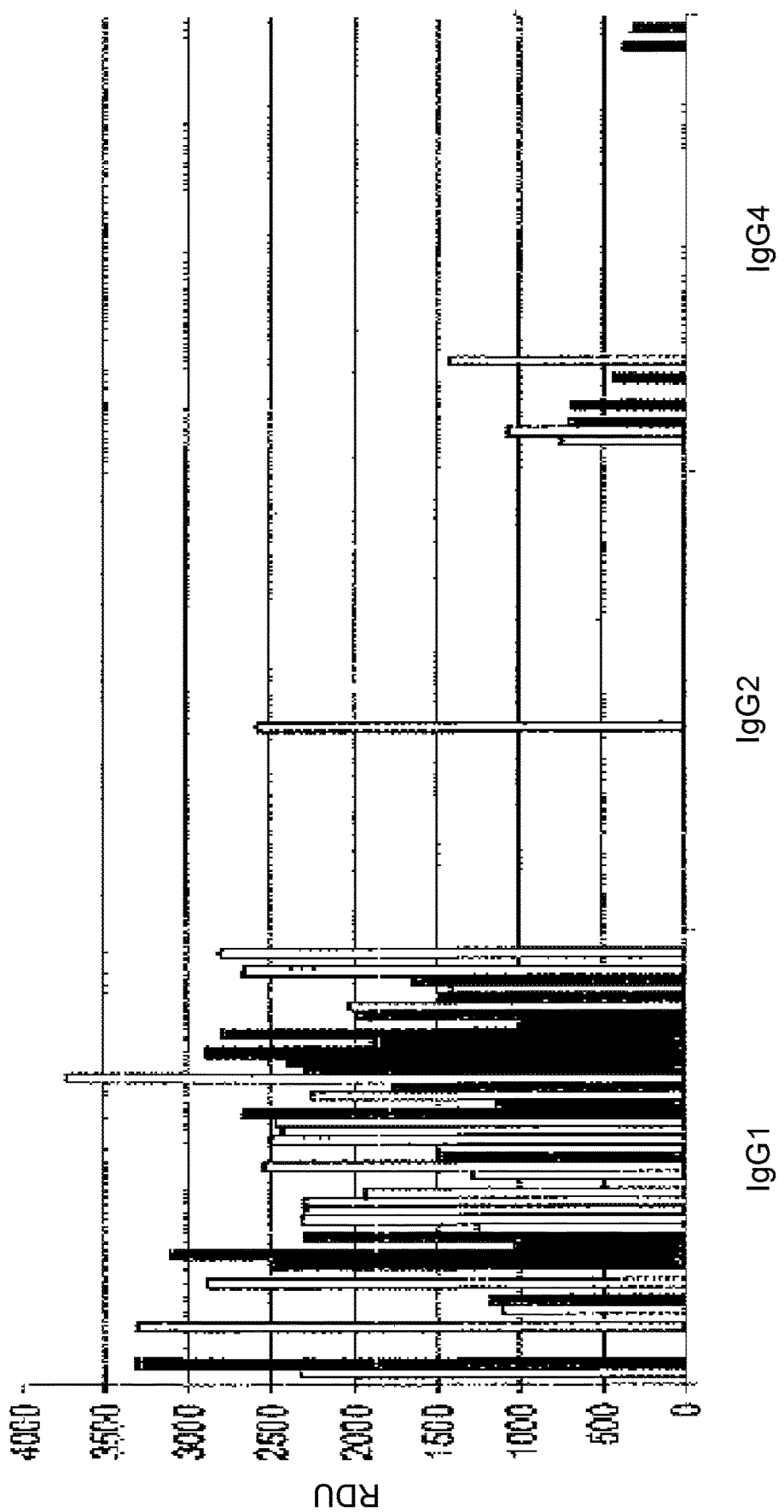
Figure 6C:
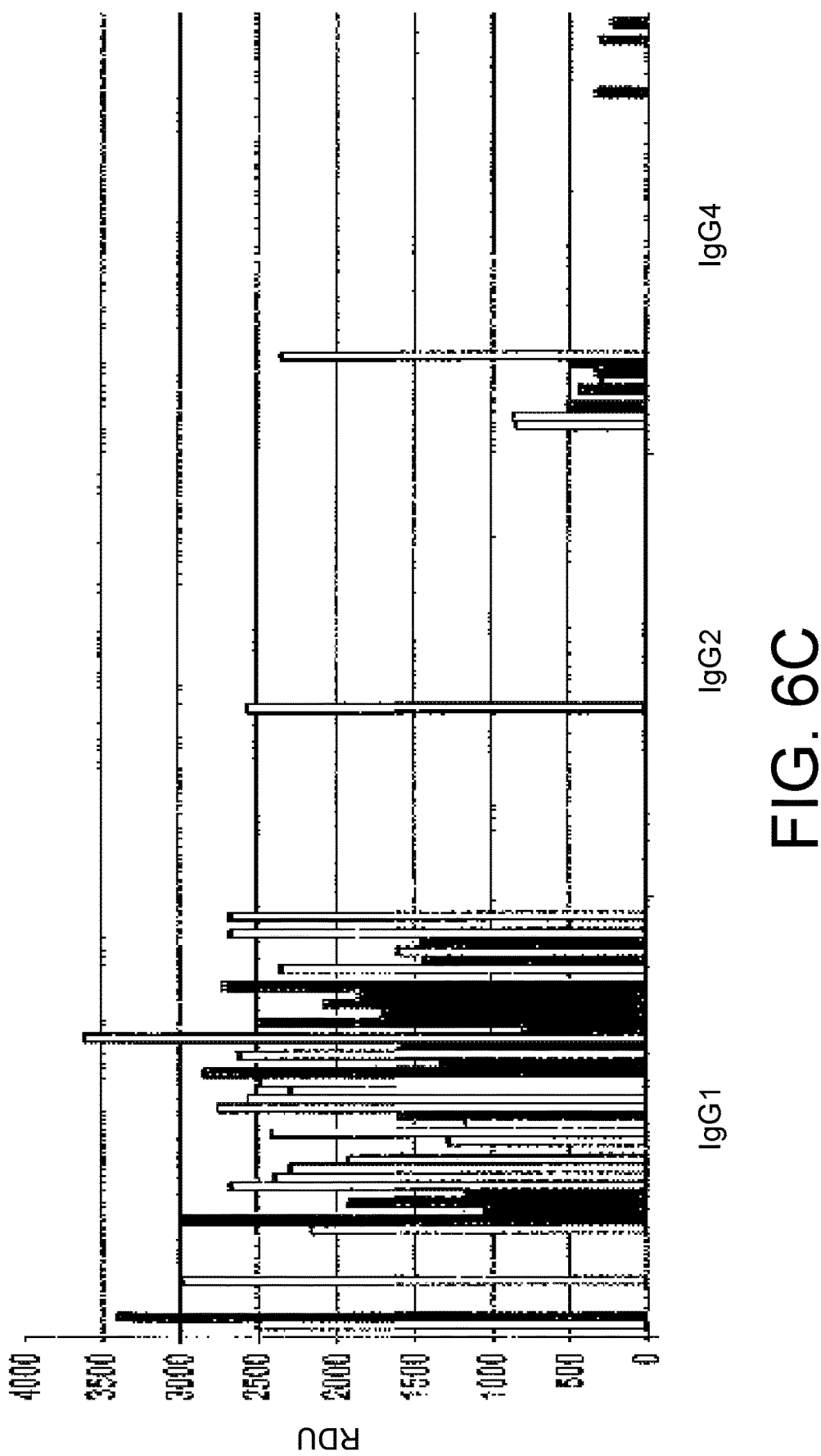

The data in FIG. 6 and Table 2 show switching of IgG subclasses in a patient. At year one, IgG3 predominated. Subsequent samples from the same patient show that IgG3 production was diminished, and instead IgG1 predominated. Further at subsequent time points a new IgG2 antibody was produced.

The data show maturation and change of production among the IgG subclasses in a single patient. This result is quite important since HLA specificities are listed nationally in UNOS, and are considered unacceptable if donor HLA mismatches occur. Clearly, some of the HLA specificities are unacceptable (i.e., IgG1 and IgG3) while other HLA specificities are acceptable (i.e., IgG2 and IgG4).

Data also show that one subject having certain HLA class I antigens produced different IgG subclass patterns temporally. Beads displaying HLA-B13 antigen bound to IgG1 in each of the three sera; beads displaying HLA-A25 antigen bound to IgG4 in each of the sera; and beads displaying HLA-B45 bound to IgG2 in each of the sera.

Types of beads displaying antigens bound to particular IgG subclasses in patterns that varied temporally with the patient. Data show that IgG3 bound to a bead displaying HLA-B41 in serum V2755, and IgG1 bound to that bead in sera V15809 and V29613 (Table 2 and FIG. 6). At the initial time point IgG3 predominated. In subsequent years, this patient expressed predominantly IgG1 and IgG4.

TABLE 2

HLA and IgG subclass analysis of three sera from one patient sampled yearly (RDU values)

| serum V2755 | | | | | serum V15809 | | | | serum V29613 | | | |
|---|---|---|---|---|---|---|---|---|---|---|---|---|
| HLA | IgG 1 | IgG2 | IgG3 | IgG4 | HLA | IgG 1 | IgG2 | IgG4 | HLA | IgG 1 | IgG2 | IgG4 |
| A25 | | | | 145 | A1 | 2332 | | | A1 | 2509 | | |
| A3 | | | | 133 | A11 | 3326 | | | A11 | 3408 | | |
| B13 | 2682 | | | | A25 | | 751 | | A25 | | | 844 |
| B27 | 111 | | | | A26 | | 1061 | | A26 | | | 868 |
| B38 | | | 1119 | | A29 | | 692 | | A29 | | | 516 |
| B39 | | | 1333 | | A3 | 3301 | | | A3 | 2985 | | |
| B41 | | | 1377 | | A30 | | 675 | | A30 | | | 442 |
| B42 | | | 1520 | | A31 | 1111 | | | A31 | | | 291 |
| B45 | | 2351 | | | A33 | 1178 | | | A34 | | | 325 |
| B51 | | | 1117 | | A34 | | 427 | | A43 | | | 480 |
| B52 | | | 1178 | | A36 | 2882 | | | A66 | | | 2356 |
| B54 | | | 1071 | | A66 | | 1418 | | A80 | 2157 | | |
| B55 | | | 1201 | | A80 | 2514 | | | B13 | 2987 | | |
| B56 | | | 1445 | | B13 | 3113 | | | B18 | 1050 | | |
| B57 | | | 1664 | | B18 | 1033 | | | B27 | 1913 | | |
| B59 | | | 1520 | | B27 | 2296 | | | B35 | 1163 | | |
| B61 | 1089 | | | | B35 | 1245 | | | B38 | 2682 | | |
| B62 | | | 1153 | | B38 | 2316 | | | B39 | 2400 | | |
| B63 | | | 1072 | | B39 | 2302 | | | B41 | 2302 | | |
| B64 | | | 1801 | | B41 | 2290 | | | B42 | 1910 | | |
| B65 | | | 2604 | | B42 | 1946 | | | B45 | | 2568 | |
| B67 | | | 1484 | | B45 | | | 2572 | B46 | 1287 | | |
| B7 | 1053 | | | | B46 | 1272 | | | B48 | 2421 | | |

Amounts of IgG subclasses were further correlated to clinical analysis of humoral rejection. IgG3 was observed to correlate with strong CF and strength of phagocytosis, followed by IgG1 and IgG2; IgG4 is a blocking antibody. Sera patterns similar to those observed in sera V15809 and V29613, having IgG3 would be more likely to fix complement and show a higher level of phagocytosis. Conversely in sera with higher amounts of IgG4 specificities a donor mismatch for these HLA antigens specificities would have no complement fixing activity and poor phagocytosis. These results indicate the importance of periodic monitoring of recipient candidate sera. Periodic monitoring and use of the methods herein are particularly important, since sensitized patients have average waiting time to transplant of 1600 days nationally.

Example 8. Correlations with Clinical Outcomes in Heart Transplant Recipients DSA and IgG subclass analysis in heart transplant (HRTX) sera was correlated with observed clinical results in four patients (Table 3). Data show that the HRTX sera of each of the four patients had DSA specific for HLA Class II antigens and each also had high levels of IgG1, indicating that most of the DSA were IgG1. Data show that the HRTX patient N1479WG had very high DSA and IgG1 and was observed to have suffered loss of his graft (Table 3), a negative outcome.

Patient N1710LF had higher DSA specific to HLA Class II antigens, and also a combination of IgG1, IgG2 and IgG4 that bound the HLA class II antigen. The IgG4 quantity was greater than that for the total IgG1 and IgG2. This patient having a high amount of IgG4 relative to both IgG1 and IgG2, and no detectable IgG3 was observed to respond well to plasma pheresis (PPh) treatment (Table 3), and was able to return home, a very positive outcome.

TABLE 3

Correlations of DSA and IgG subclasses in HRTX sera and transplant (RDU values)

| HRTX serum | DSA | IgG1 | IgG2 | IgG3 | IgG4 | result observed |
|---|---|---|---|---|---|---|
| N1424AB | DR7 (weak), DQ2 (7,000) | DQ2 (3,000) | — | — | — | PPh, improving |
| N1479WG | DQ4 (10,000) | DQ4 (5,000) | — | — | — | graft loss |
| N1661SJ | DQ4 (1,000), DQ6 (4,000) | DQ6 (4,000) | — | — | — | PPh, stable |
| N1710LF | DQ2 (11,000) | DQ2 (3,000) | DQ2 (2,000) | — | DQ2 (7,000) | PPh, to home |

PPh indicates plasma pheresis

HRTX patient N1710LF was tested as a function of time and was observed to have strong DSA and IgG subclass response to HLA class II antigens. Further analysis of this pattern showed IgG subclass switching to IgG4 blocking antibodies (Table 4). Data also show that IgG1 and IgG3 amounts decreased as a function of time during four months. IgG2 was not observed in this patient.

The methods described herein surprisingly can be correlated to serve as diagnostic and prognostic techniques. These methods are a powerful addition to data obtained by other methods, such as analysis of C4d.

ment receptors), the presence of which affect cross matching analysis to improve data by lowering non-specific binding.

False positive results for flow cytometry cross matching remain a significant problem. These erroneous results are caused by passive binding by immunoglobulin and to Fc receptors such as CD32 and complement receptors such as CD35 and CD21. B cells have a high density of both CD35 and CD21 receptors. CD35 binds to directly to C3b and CD21 binds degradation products of C3b. Antibody antigen complexes (immune complexes with C3b) bind to CD35 and CD21 causing false positive reactions. C3b is a key component of the complement system that binds to pathogens resulting in greater internalization by phagocytic cells. Variable expression of HLA negatively affects predictability and usefulness of cross matching (XM) results. Thus, there is a need for an accurate method of XM.

Cells were treated with Pronase, a proteolytic enzyme, for 30 min at 37° C. at a concentration of 2.4 units/ml (0.5 mg/ml; Sigma Aldrich, catalogue number P5147). A control sample of cells was not treated with Pronase. Direct quantitation of the fluorescence intensity of samples was obtained using a calculation of "molecules equivalent soluble fluorescence" (MESF units). Results were obtained for complement receptors CD35, CD21, Fc-gamma receptors (CD32),

TABLE 4

Analysis of DSA and immunoglobulin subclasses in a successful HRTX recipient as a function of time (RDU values)

| time | DSA | IgG1 | IgG2 | IgG3 | IgG4 | antibody subclass clinical prediction |
|---|---|---|---|---|---|---|
| month one | DQ2 (16000), DR53(weak) DPAs | DQ2 (2446) | — | DPA1 (1909) | DQ2 (5465), DR53 (394) | stable |
| month two | DQ2 (16000), DR53 (weak), DPAs | DQ2 (1893) | — | DPA1 (1464) | DQ2 (4971), DR53 (360) | stable |
| month four | DQ2 (16000) DR53 (weak), DPAs | DQ2 (1303) | — | DPA1 (1218) | DQ2 (4742), DR53 (396) | stable |

Example 9. Comparison of Complement Receptors, Fc Receptors and HLA on Cells Treated with Enzymes Enzyme digestion was tested as a method to reduce or eliminate cell surface proteins (e.g., Fc receptors, compleand HLA Class I and II alleles. Data for kinetics of PD was also obtained. Statistical analysis included paired sample t-test.

Figure 7A:
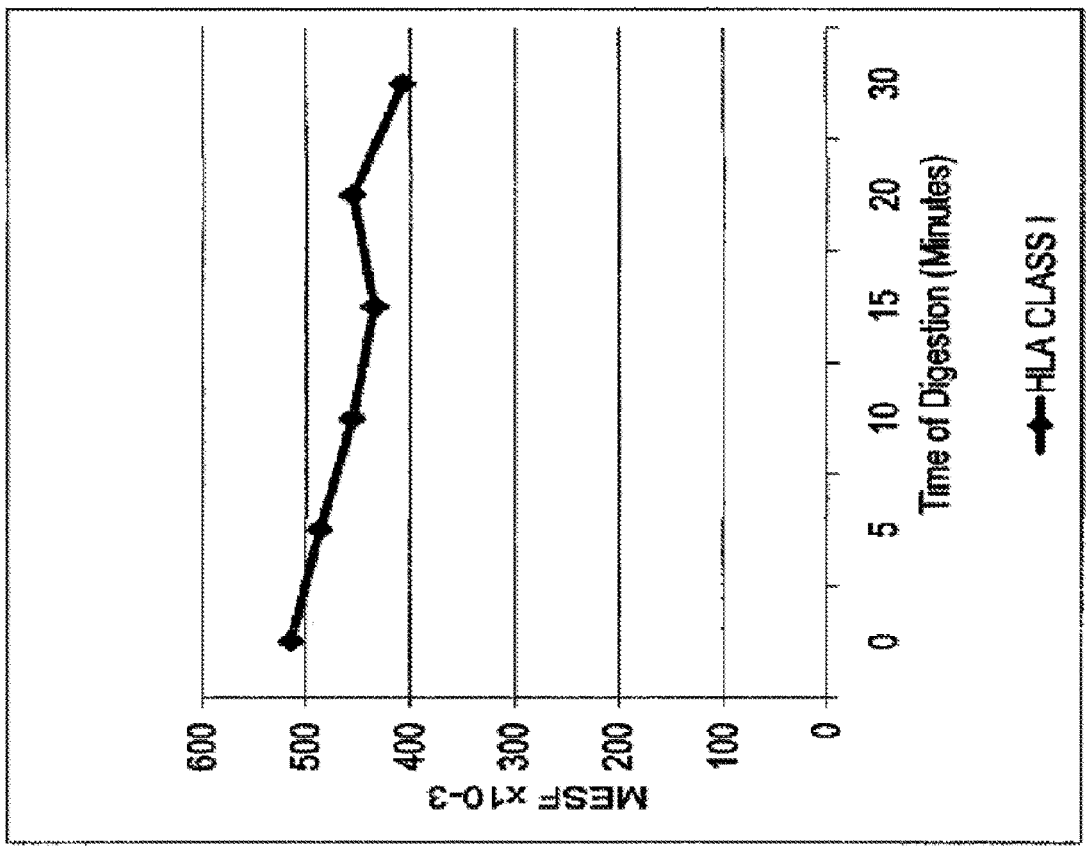
FIG. 7A and FIG. 7B are a set of line graphs showing units of molecule equivalent soluble fluorescence (MESF ordinate) on the ordinate of amount of surface proteins on cells, which were enzymatically digested with Pronase as a function of time on the abscissa (minutes).
Figure 7B:
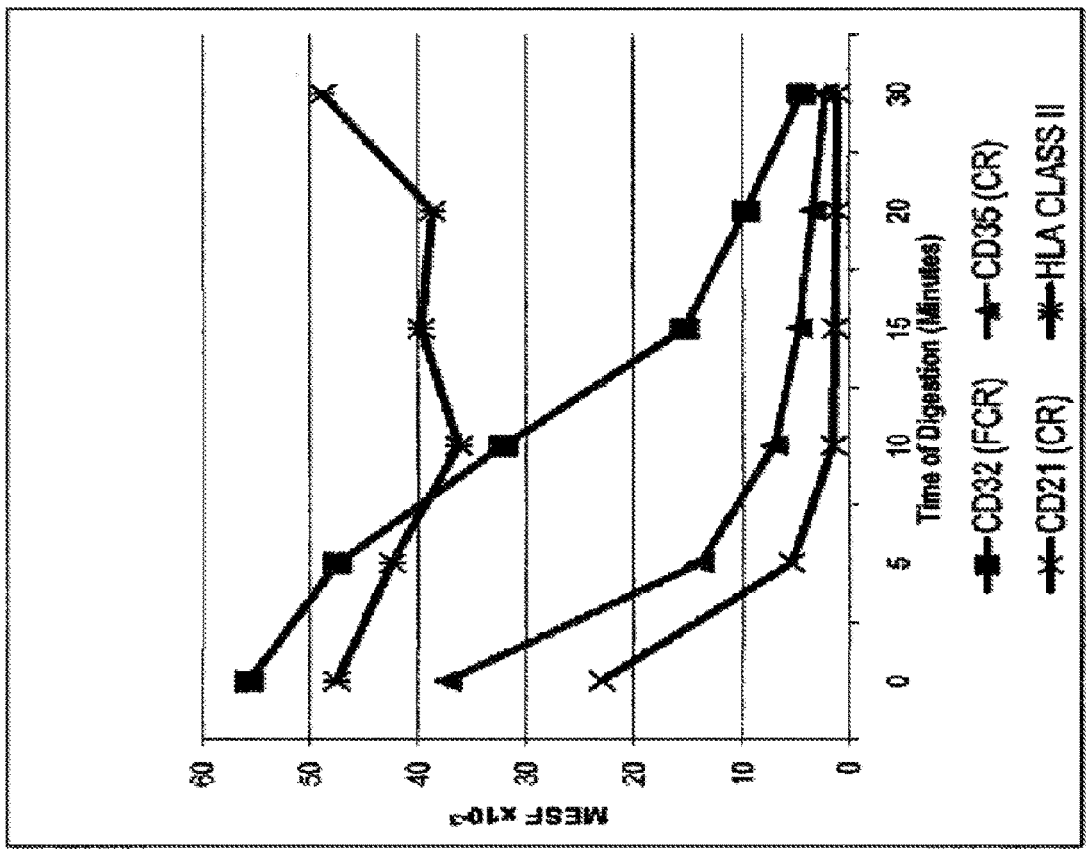

Results show a gradual loss of HLA class I proteins as a function of time for cells treated with Pronase. MESF units decreased by 20% at 30 min of PD, indicating 20% less HLA class I protein (FIG. 7 panel A). A slight increase was observed in MESF units for HLA class II antigens, and greater than a 90% decrease in MESF units for complement receptors CD21 and CD35 and Fc receptor CD32 (FIG. 7 panel B). The data show a wide variation in HLA expression between class I and class II. Amount of HLA class I was almost an order of magnitude greater than for HLA class II.

Furthermore, antibodies specific for HLA Class I antigens (HLA-ABC) showed four-fold variation of expression among strains of cells. PBL were observed to have higher MESF units than cells from spleen or nodes. Pronase did not cause a significant change in expression (FIG. 8 panel A).

Figures 8A, 8B:
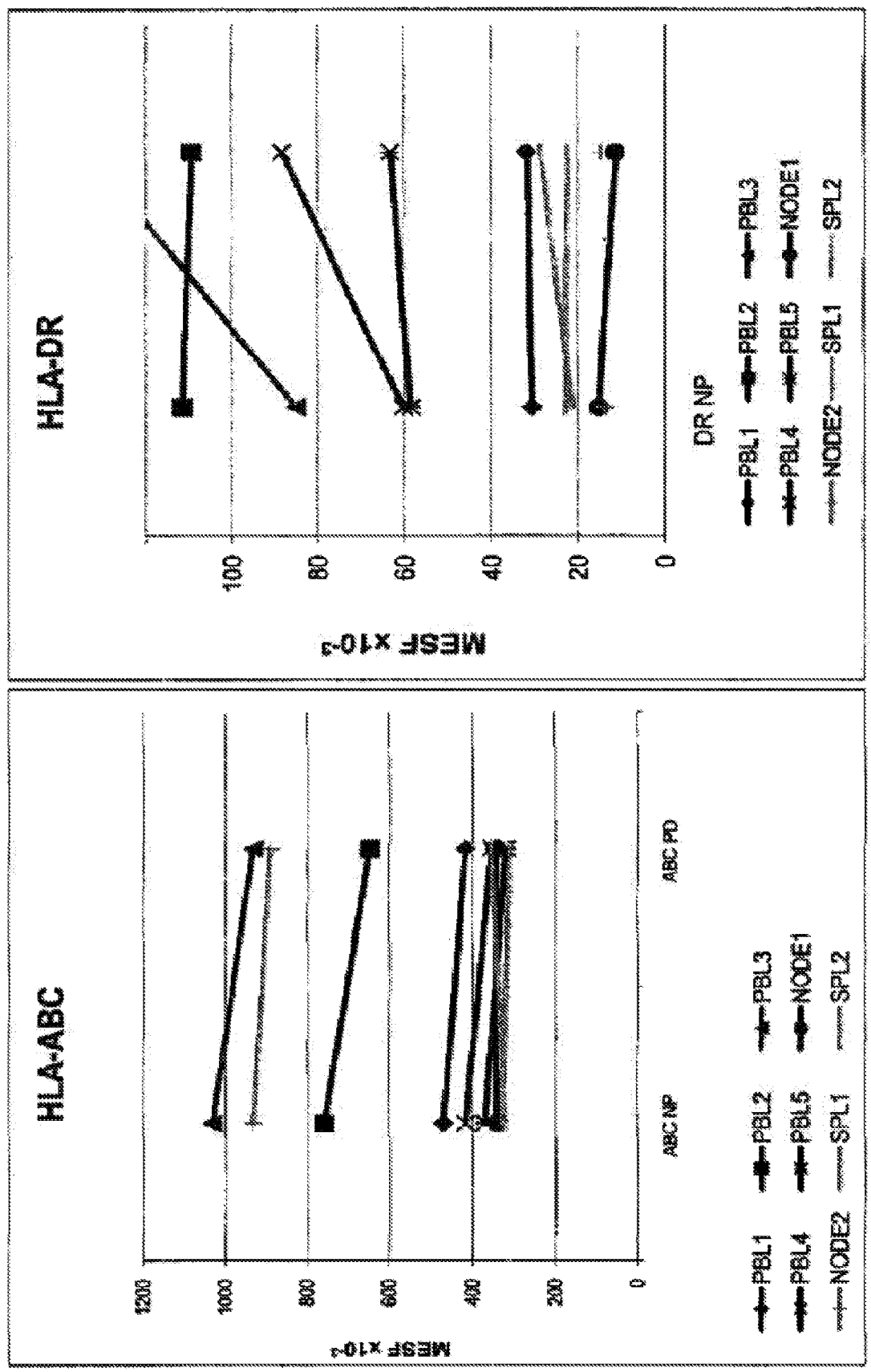
FIG. 8A and FIG. 8B are a set of line graphs showing HLA class (panel A) and class II (panel B) antigens on cells that were enzymatically digested (PD) using Pronase (data points on right), and on control cells not digested (NP, data points on left) in MESF units. Cells were peripheral blood lymphocytes (PBL), spleen B lymphocytes (SBL), and node B lymphocytes (NBL).
Figure 10A:
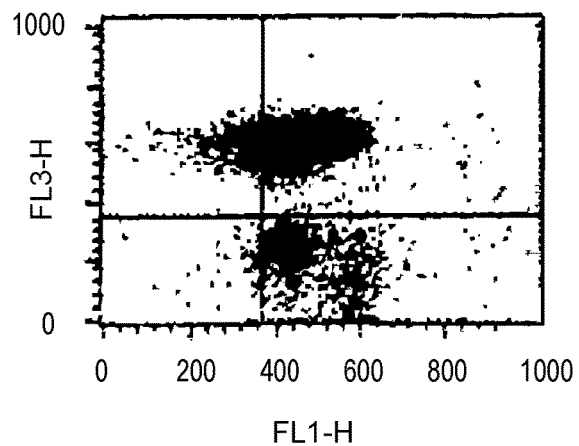
FIG. 10A, FIG. 10B, FIG. 10C and FIG. 10D are a set of three color flow cytometry crossmatch data of a CD55 (DAF) surface protein observed on a cell sample that was digested with Pronase.
Figure 10B:
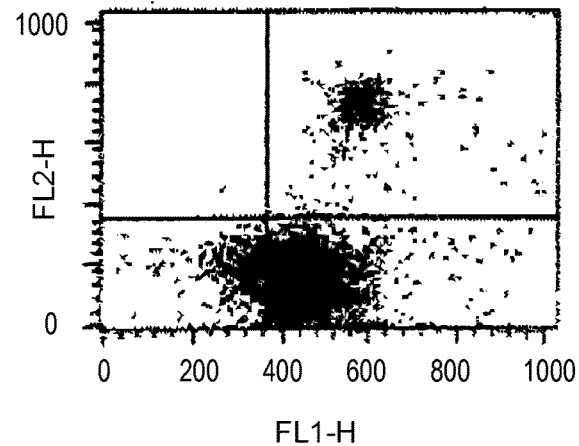
Figure 10C:
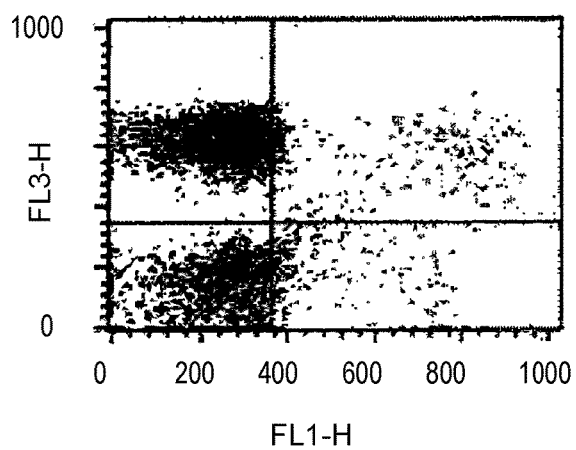
Figure 10D:
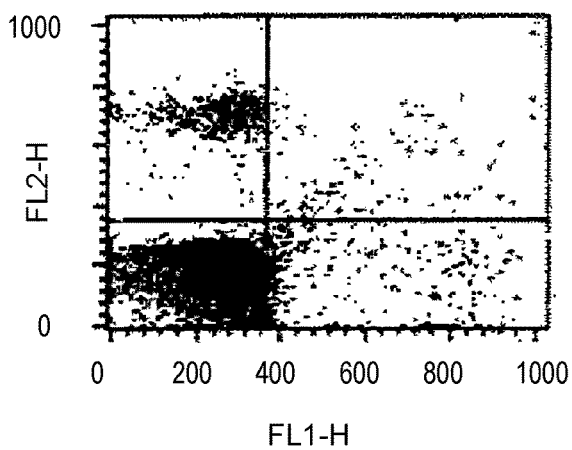

Antibodies that specifically bind to a HLA class II antigen HLA-DR were observed to have about 10 fold lower expression compared to antibodies specific for the HLA class I antigen (FIG. 8 panels A and B). Pronase treatment resulted in increased MESF units indicating increased binding. These data show that Pronase exposes HLA Class II binding sites (FIG. 8 panel B).

For CD32, a 50% to 75% decrease, and for CD35 a 75% to 95% decrease in MESF units was observed following Pronase treatment, compared to controls not treated (FIG. 9 panels A and B). Data show that the receptors tested, CD20, CD19, CD21, CD32, and CD35, were sensitive to Pronase treatment. However HLA was not as sensitive as these other receptors to Pronase digestion at the tested concentration (0.5 mg/ml). Cell death was observed in B cells treated with a higher concentration (1.5 mg/ml) of Pronase. Titrating the concentration of Pronase to test different proteolytic enzymes was performed to optimize reduction of non-specific binding.

A wide variation in HLA expression between Class I and Class II was observed in cells treated with enzymatically digested Pronase. B cells showed 10-fold less HLA-Dr compared to HLA-ABC. Enzymatic digestion with Pronase was effective in eliminating cell surface proteins including Fc receptors and complement receptors. HLA antigens were more difficult to remove. These data show that differential HLA expression and FcR and Cr binding affects the specificity and background in the XM method. Methods for using enzymatic digestion, for example a proteolytic enzyme such as Pronase are useful for cytometry cross matching for characterizing a profile of donor candidates.

Complement decay-accelerating factor (DAF), also known as CD55, was completely removed from the cell surface by Pronase (FIG. 10). The digestion clearly shifts the distribution of cells from right quadrants to left quadrants, indicating that CD55 (DAF) was completely removed. Protectin (CD59) was partially degraded and was removed from the cell surface by Pronase (FIG. 11). CD59 is bound to the cell surface with a glycolipid bond, therefore this cell surface protein would be further removed by a combination of proteolytic digestion and lipase treatment.

Examples herein show a method for enzymatic treatment of cells, to facilitate use of human serum as a complement source. The method described uses antibodies specific for receptors as controls, for example monoclonal antibodies specific for CD55, CD59, and CD46.

What is claimed is:

1. A kit for generating a time series of quantified amounts of IgG1 and IgG4 for a subject comprising:
   beads for generating the time series;
   human leucocyte antigens for generating the time series that comprise at least one human leucocyte antigen bindable by IgG1 and at least one human leucocyte antigen bindable by IgG4;
   at least one monoclonal anti-subject antibody capable of specifically binding to IgG1 and at least one monoclonal anti-subject antibody capable of specifically binding to IgG4 for generating the time series;
   detectable labels for generating the time series, wherein a human subject sample that comprises IgG1 and IgG4 forms bead bound complexes detectably labeled to quantify an amount of the IgG1 and an amount of the IgG4 in the human subject sample; and
   instructions for use to relate the time series of quantified amounts of IgG1 to C4d reactivity and quantified amounts of IgG4 to at least one blocking function and to relate the time series to a transplantation prognosis of the subject.

2. The kit according to claim 1, further comprising a negative control comprising at least one structure absent antigen.

3. The kit according to claim 1 wherein the monoclonal anti-subject antibody is a murine anti-human antibody.

4. The kit according to claim 3, wherein the detectable labels comprise an anti-murine antibody.

5. The kit according to claim 4, wherein the anti-murine antibody is obtained from at least one immunized animal selected from a group consisting of: caprine, lapine, equine, feline, canine, bovine, and ovine.

6. The kit according to claim 1, wherein the detectable labels comprise a tag selected from the group of colorimetric, fluorescent, radioactive, and affinity labels.

7. The kit according to claim 1, wherein the detectable labels comprise phycoerythrin.

8. The kit according to claim 1, comprising instructions for use for prognosing or diagnosing a human subject for transplant suitability or diagnosis or prognosis of allergy and autoimmune disease using the time series.

9. The kit according to claim 1, wherein at least a portion of the beads comprise an internal dye and an amino acid sequence from a subclass or an isotype of an MHC antigen.

10. The kit according to claim 1, comprising at least one enzyme that removes a subset of cell surface proteins.

11. The kit according to claim 10, wherein the at least one enzyme comprises a proteolytic enzyme.

12. The kit according to claim 11, wherein the proteolytic enzyme is selected from at least one member of a group of consisting of: serine proteinases, cysteine proteinases, aspartic proteinases, and metalloproteinases.

13. The kit according to claim 1, wherein the human leucocyte antigens (HLAs) are obtained from a plurality of subclasses and isotypes of major histocompatibility complex (MHC) proteins.

14. The kit according to claim 13, wherein the HLAs comprise a HLA class I antigen that is selected from a group consisting of: antigen A, antigen B, and antigen C.

15. The kit according to claim 13, wherein the HLAs comprise a HLA class II antigen that is selected from a group consisting of: antigen DR, antigen DP, and antigen DQ.

16. The kit according to claim 1, comprising instructions of use to analyze for donor specific antibodies (DSA).

17. The kit according to claim 1, comprising complement fixation (CF) detection materials.

18. The kit according to claim 1 wherein one of the bead bound complexes comprises one of the beads, one of the human leucocyte antigens, one of IgG1 and IgG4 of the human subject sample, one of the monoclonal anti-subject antibodies, and one of the detectable labels.

19. The kit according to claim 18 wherein the one of the monoclonal anti-subject antibodies is a murine monoclonal anti-subject IgG and wherein the one of the detectable labels comprises an anti-murine IgG F(ab)2.

20. The kit according to claim 1 wherein the generated time series comprises a function of quantified amounts of IgG1 with respect to time and a function of quantified amounts of IgG4 with respect to time, wherein the functions are indicative of the transplantation prognosis of the subject.

* * * * *